（12）United States Patent
Verkhusha et al.

US010968256B2

(10) Patent No.: US 10,968,256 B2
(45) Date of Patent: Apr. 6, 2021

(54) OPTOGENETIC SYSTEM BASED ON BACTERIAL PHYTOCHROME CONTROLLABLE WITH NEAR INFRA-RED LIGHT

(71) Applicant: Albert Einstein College of Medicine, Bronx, NY (US)

(72) Inventors: Vladislav V. Verkhusha, Bronx, NY (US); Andrii A. Kaberniuk, Bronx, NY (US); Anton A. Shemetov, New York, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 383 days.

(21) Appl. No.: 15/761,598

(22) PCT Filed: Sep. 29, 2016

(86) PCT No.: PCT/US2016/054322
§ 371 (c)(1),
(2) Date: Mar. 20, 2018

(87) PCT Pub. No.: WO2017/059002
PCT Pub. Date: Apr. 6, 2017

(65) Prior Publication Data
US 2018/0346523 A1 Dec. 6, 2018

Related U.S. Application Data

(60) Provisional application No. 62/235,828, filed on Oct. 1, 2015.

(51) Int. Cl.
*C07K 14/195* (2006.01)
*A61N 1/39* (2006.01)
*A61H 31/00* (2006.01)
*A61K 41/00* (2020.01)

(52) U.S. Cl.
CPC ......... *C07K 14/195* (2013.01); *A61H 31/005* (2013.01); *A61H 31/007* (2013.01); *A61K 41/0042* (2013.01); *A61N 1/3937* (2013.01); *A61N 1/3993* (2013.01); *A61H 2201/10* (2013.01); *A61H 2201/5007* (2013.01); *A61H 2201/5043* (2013.01); *A61H 2201/5084* (2013.01); *A61H 2201/5097* (2013.01); *A61H 2230/06* (2013.01); *C07K 2319/00* (2013.01); *C07K 2319/60* (2013.01); *C07K 2319/80* (2013.01)

(58) Field of Classification Search
None
See application file for complete search history.

(56) References Cited

U.S. PATENT DOCUMENTS

2011/0099646 A1  4/2011  Lacoste et al.

OTHER PUBLICATIONS

PCT International Search Report and Written Opinion dated Jan. 23, 2017 for PCT International Patent Application No. PCT/US2016/054322, 16 pages.
Bellini, D et al., Structure of a Bacteriophytochrome and Light-Stimulated Protomer Swapping with a Gene Repressor., Structure, Jul. 12, 2012; vol. 20, No. 8; pp. 1436-1446.
Braatsch, S et al., The O2-Responsive Repressor PpsR2 but not PpsR1 Transduces a Light Signal Sensed by the BphP1 Phytochromein Rhodopseudomonas palustris CGA009, FEMS Microbiology Letters, Apr. 24, 2007; vol. 272, No. 1; pp. 60-64.
Piatkevich, K D et al., Engineering of Bacterial Phytochromes for Near-Infrared Imaging, Sensing, and Light-Control in Mammals, Chemical Society Reviews, Jan. 29, 2013; vol. 42, No. 8; pp. 1-18.
Braatsch, S et al., Rhodopseudomonas palustris CGA009 Has Two Functional ppsR Genes, Each of Which Encodes a Repressor of Photosynthesis Gene Expression, Biochemistry, Dec. 5, 2006; vol. 45, No. 48; pp. 14441-14451.
Muller, K et al., A Red/Far-Red Light-Responsive Bi-Stable Toggle Switch to Control Gene Expression in Mammalian Cells, Nucleic Acids Research, Jan. 25, 2013; vol. 41, No. 7; pp. 1-11.
Kaberniuk, A A et al., An Optogenetic System Based on Bacterial Phytochrome Controllable with Near-Infrared Light, Nature Methods, May 9, 2016; vol. 13, No. 7; pp. 1-20.
PCT Notification Concerning Transmittal of International Preliminary Report on Patentability dated Apr. 3, 2018 in connection with PCT International Application No. PCT/US2016/054322, 12 pages.

Primary Examiner — Channing S Mahatan
(74) Attorney, Agent, or Firm — Fox Rothschild LLP

(57) ABSTRACT

A novel optogenetic system, including constructs and methods, is provided based on the interaction of *Rhodopseudomonas palustris* BphP1 and *Rhodopseudomonas palustris* PpsR2 or a non-dimerizing variant thereof.

15 Claims, 21 Drawing Sheets

Specification includes a Sequence Listing.

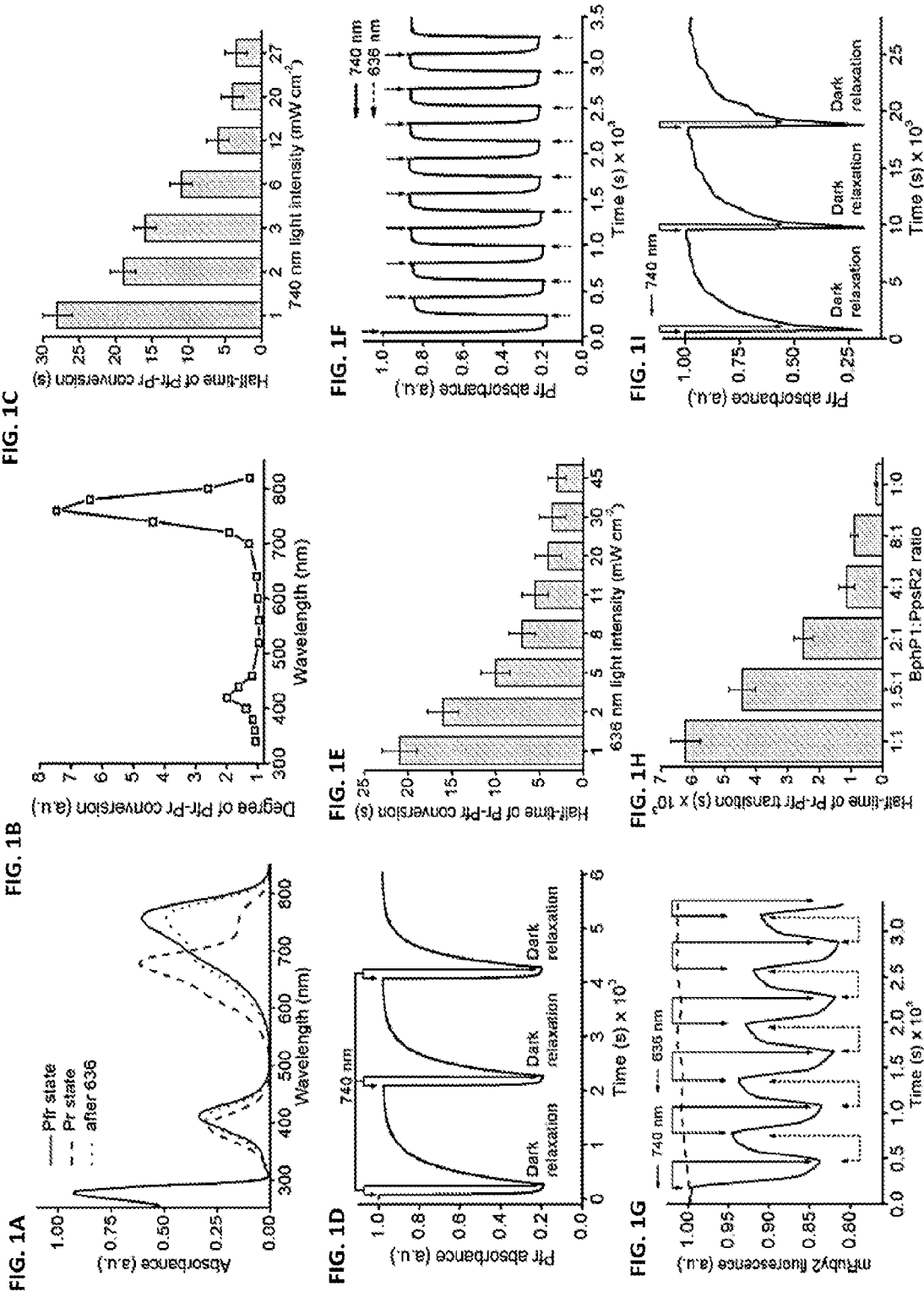

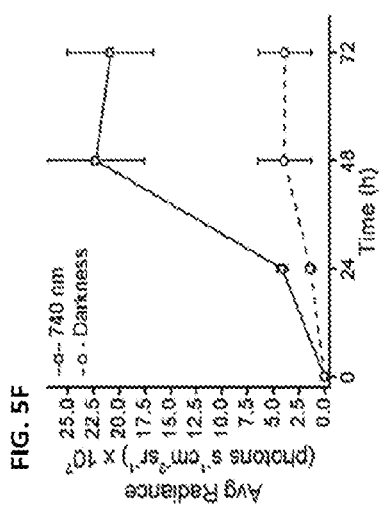
FIG. 5A
FIG. 5B
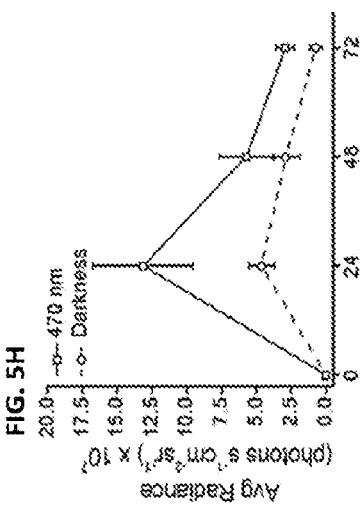
FIG. 5C
FIG. 5D
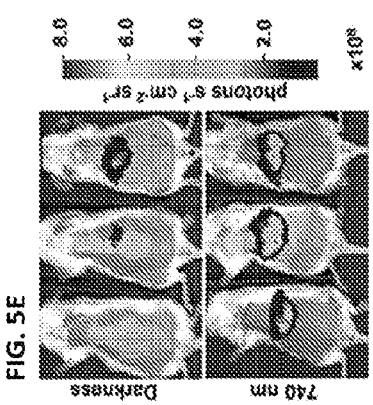
FIG. 5E
FIG. 5F
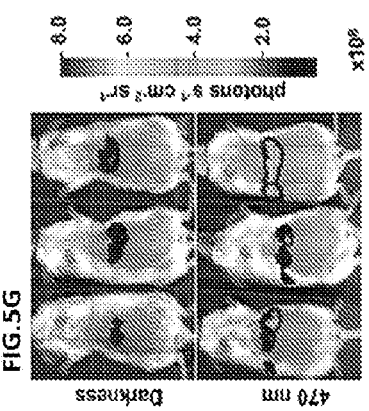
FIG. 5G
FIG. 5H
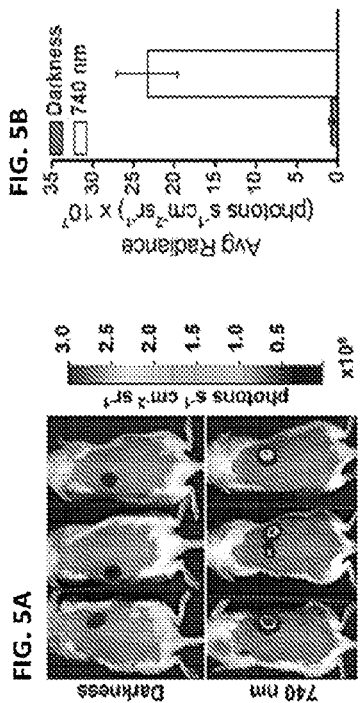
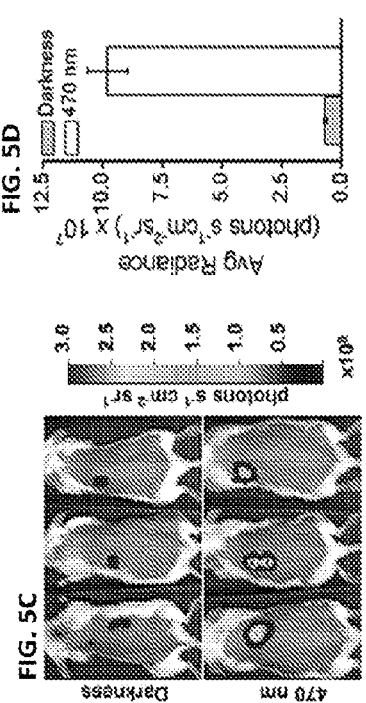

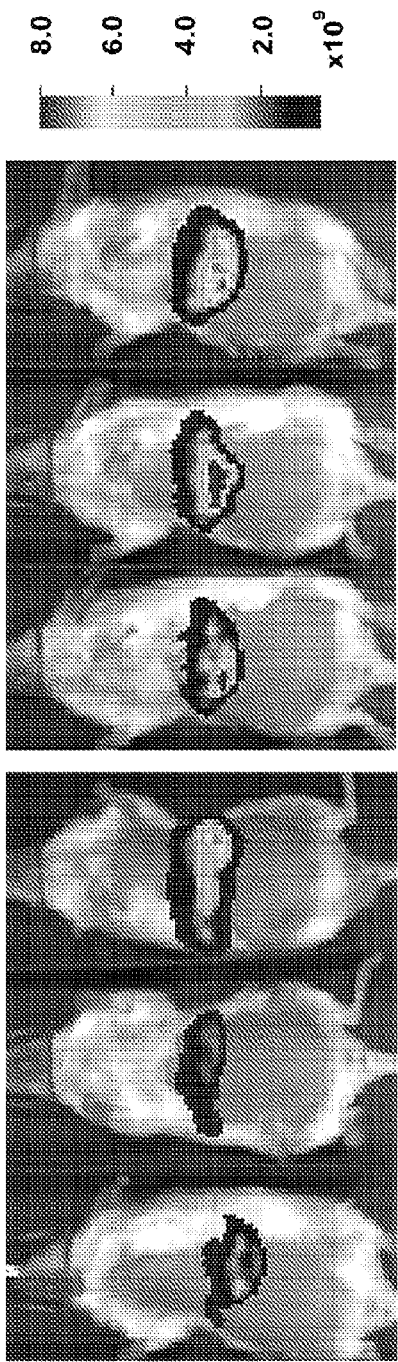
FIG. 20A
FIG. 20B
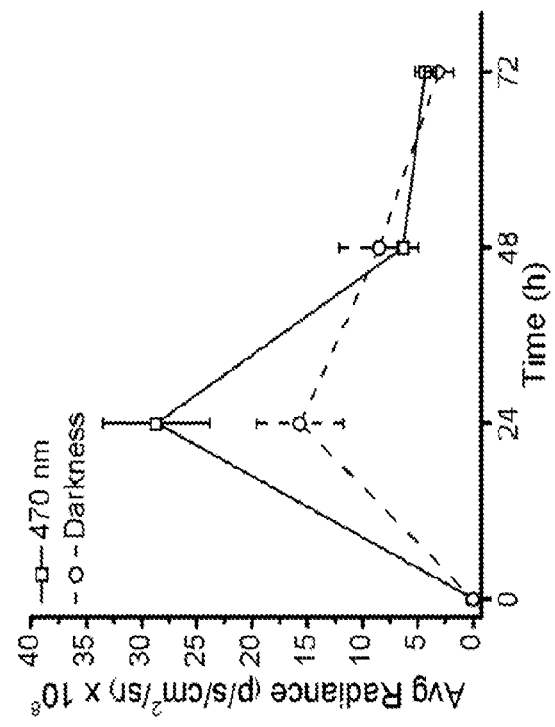
FIG. 20C

OPTOGENETIC SYSTEM BASED ON BACTERIAL PHYTOCHROME CONTROLLABLE WITH NEAR INFRA-RED LIGHT

CROSS-REFERENCE TO RELATED APPLICATIONS

This application is a U.S. national stage entry under 35 U.S.C. § 371 of PCT International Patent Application No. PCT/US2016/054322, filed Sep. 29, 2016, which claims benefit of U.S. Provisional Application No. 62/235,828, filed Oct. 1, 2015, the contents of each of which are incorporated herein by reference into the subject application.

This invention was made with government support under grant numbers GM073913, GM108579 and CA164468 awarded by the National Institutes of Health. The government has certain rights in the invention.

BACKGROUND OF THE INVENTION

Throughout this application various patents and other publications are referred to by number in parenthesis. Full citations for the references may be found at the end of the specification. The disclosures of these references and all patents, patent application publications and books referred to herein are hereby incorporated by reference in their entirety into the subject application to more fully describe the art to which the subject invention pertains.

Precise spatiotemporal control of biochemical processes in live cells and animals will advance basic biology and biomedicine. A promising approach to provide such control is optogenetics, a field of biology focused on controlling desired cell functions utilizing light as an activation signal. Among several directions of optogenetics, the important one is a modulation of protein-protein interactions (PPIs) that regulate specific cellular pathways. The PPI optogenetic tools consist of fusions between the target proteins and the chromophore-containing protein domains capable of light-induced homo- or heterodimerization. Light-dependent genetically encoded systems exhibit several advantages over pharmacologically-based PPI constructs due to their non-invasiveness, high PPI activation rates, and absence of side effects caused by drugs.

Several genetically encoded PPI optogenetic systems have been engineered using different families of photoreceptors, such as LOV (light/oxygen/voltage) domains, BLUF (blue light utilizing FAD) domains (1), cryptochromes and subclass of phytochromes, such as plant phytochromes (1, 2, 3). Although use of these systems in cultured mammalian cells has been shown, their application in living mammals could be complicated because of several factors.

First, a range of wavelengths where light exhibits maximum depth of tissue penetration due to low light-scattering and minimal absorbance of melanin, hemoglobin and water lies between 650 and 900 nm, and is called a near infra-red (NIR) tissue transparency window (4). The LOV, BLUF and cryptochrome-based optogenetic systems sense light in blue region of spectrum. Only phytochrome photoreceptors are activated with far-red or NIR light. Second, different phytochrome subfamilies incorporate different chromophores. Phytochromobilin and phycocyanobilin serve as chromophores in plant phytochromes, whereas bacterial phytochromes incorporate biliverdin IXα (BV) (4, 5, 6). These chromophores are products of heme degradation. A chromophore is autocatalyticaly and covalently attached via a thioether bond between the A-ring of tetrapyrrole and conserved cysteine residue of the phytochromes (6-8). Importantly, among these tetrapyrroles, BV exhibits the most NIR-shifted spectra of its absorption. Third, a use of the plant phytochrome based PPI optogenetic systems is limited by the requirement of exogenously supplied phycocyanobilin chromophore, which is unavailable in eukaryotic cells and organisms, including mammals (9). In contrast, the BV chromophore utilized by bacterial phytochromes is abundant in animal cells, and thus its exogenous supply is not required (10). This latter feature was used to engineer bacterial phytochromes into several types of NIR probes for mammalian tissues including permanently fluorescent proteins (11), photoactivatable fluorescent proteins (12) and PPI reporters (13).

Bacterial phytochromes are natural dimeric photoreceptors that control gene expression and second messenger signaling in bacteria in response to NIR light (14). They consist of a photosensory core module and an output effector module, which is represented by histidine kinase in canonical bacterial phytochromes, and by other domains in non-canonical ones. Spectral properties are defined by a photosensory core module where the protein-chromophore interaction occurs (5, 15, 16). Within a chromophore-binding pocket BV can adopt two conformational states, termed Pr and Pfr and absorbing far-red and NIR light, respectively. Isomerization of BV chromophore between Pr and Pfr states causes conformational changes in the protein backbone and activation of an effector module (17). Replacement of natural effector modules with phosphodiesterase and adenylate cyclase allows for modulating levels of cyclic nucleotides (18-20). Most of bacterial phytochromes undergo photoconversion from a Pr state to the Pfr state with 660-700 nm light. However, there is a small group, termed bathyphytochromes, which adopts Pfr as a ground state and undergoes Pfr→Pr photoconversion upon 740-780 nm light irradiation (21). Upon photoactivation, bacterial phytochromes can be converted back to the ground state either with light, which is absorbed by the activated state, or by means of thermal relaxation in darkness.

The present invention address the need for improved methods for controllably inducing protein-protein interactions or controllably inducing gene expression using convenient near infrared light.

SUMMARY OF THE INVENTION

An isolated nucleic acid is provided encoding (i) a protein having the sequence of *Rhodopseudomonas palustris* BphP1 and (ii) a protein or peptide which is heterologous relative to *Rhodopseudomonas palustris*. In an embodiment, the nucleic acid is a cDNA.

Also provided is an isolated nucleic acid encoding (i) a protein having the sequence of *Rhodopseudomonas palustris* PpsR2 or a non-dimerizing variant thereof and (ii) a protein or peptide which is heterologous relative to *Rhodopseudomonas palustris*. In an embodiment, the nucleic acid is a cDNA.

Also provided is an isolated nucleic acid comprising a first and second portion, the first portion encoding a protein having the sequence of *Rhodopseudomonas palustris* BphP1 and a protein or peptide which is heterologous relative to *Rhodopseudomonas palustris*, and the second portion encoding a protein having the sequence of *Rhodopseudomonas palustris* PpsR2 or a non-dimerizing variant thereof and a protein or peptide which is heterologous relative to *Rhodopseudomonas palustris*.

A cell is provided, wherein the cell is not in a human being, transformed with the nucleic acid of as described herein.

A fusion protein is provided comprising a protein having the sequence of a *Rhodopseudomonas palustris* BphP1 and a second protein or peptide. A fusion protein is provided comprising a protein having the sequence of a *Rhodopseudomonas palustris* PpsR2 and a second protein or peptide.

A method is provided for inducing interaction of a first protein with a second protein in a system, the method comprising
providing a system comprising (a) a fusion protein comprising (i) a protein having the sequence of a *Rhodopseudomonas palustris* BphP1 and (ii) the first protein, and (b) a fusion protein comprising (i) a protein having the sequence of a *Rhodopseudomonas palustris* PpsR2 or a non-dimerizing variant thereof and (ii) the second protein, and (c) an amount of biliverdin; and
irradiating the system with near infrared light sufficient to induce interaction of a *Rhodopseudomonas palustris* BphP1 with a *Rhodopseudomonas palustris* PpsR2 or a non-dimerizing variant thereof. In embodiments, the amount of biliverdin is present endogenously, added exogenously or produced enzymatically.

Also provided is a method for inducing translocation of a predetermined protein to a predetermined location in a cell comprising
providing a system comprising (a) a fusion protein comprising (i) a protein having the sequence of a *Rhodopseudomonas palustris* BphP1 and (ii) a first protein, and (b) a fusion protein comprising (i) a protein having the sequence of a *Rhodopseudomonas palustris* PpsR2 or a non-dimerizing variant thereof and (ii) a second protein, and (c) an amount of biliverdin, wherein one of the first and second proteins is the predetermined protein and wherein the other of the first and second proteins is a protein that preferentially locates to the predetermined location in a cell; and
irradiating the system with near infrared light sufficient to induce interaction of a *Rhodopseudomonas palustris* BphP1 with a *Rhodopseudomonas palustris* PpsR2 or a non-dimerizing variant thereof.

A kit is provided comprising any of the nucleic acid, fusion protein and/or system described herein and instructions for use.

The nucleic acids, fusion proteins and methods described herein are applicable mutatis mutandis to the non-canonical BphP and PpsR2 not present in *Rhodopseudomonas palustris*.

Additional objects of the invention will be apparent from the description which follows.

BRIEF DESCRIPTION OF THE DRAWINGS

FIG. 1a-1i: Spectral properties of BphP1 and characterizations of BphP1-PpsR2 interaction in vitro. (a) Absorbance spectra of BphP1 in the Pfr state (solid line), after photoconversion to the Pr state with 740/25 nm (dashed line) and after conversion back to the Pfr state with 636/20 nm (dotted line). (b) Action spectrum of the Pfr→Pr photoconversion measured as the relative decrease of Pfr absorbance detected at 780 nm upon irradiation with light of specific wavelength. (c) Dependence of the half-time of light-induced Pfr→Pr photoconversion on the intensity of 740/25 nm light (n=3, error bars are s.e.m.). (d) Absorbance of BphP1 in the Pfr state during repeated illumination with 740/25 nm light followed by dark relaxation. (e) Dependence of the half-time of light-induced BphP1 Pr→Pfr photoconversion on the intensity of 636/20 nm light (n=3, error bars are s.e.m.). (f) Absorbance of BphP1 in the Pfr state during repeated illumination cycles with 740/25 nm light and then with 636/20 nm light. Absorbance in (b), (d) and (f) was measured at 780 nm. (g) Time-course of FRET changes during BphP1 photoswitching between the Pr and Pfr states either together with PpsR2-mRuby2 (sold line) or together with mRuby2 control (dashed line). Solid arrows correspond to 740/25 nm illumination. Dashed arrows correspond to 636/20 nm illumination. (h) Half-time of dark relaxation of BphP1 (Pr→Pfr transition) in the presence of various quantities of PpsR2-mRuby2 (n=3, error bars are s.e.m.). (i) Reversible dark relaxation cycles from the Pr to the Pfr state of a BphP1 and PpsR2 mixture with 8:1 ratio. Arrows correspond to 740/25 nm illumination.

FIG. 5a-5h: Light-induced transcription activation in mice. (a) Rluc8 bioluminescence detected in mice with subcutaneously injected HeLa cells stably expressing BphP1-mCherry-TetR and co-transfected with the NLS-PpsR2-VP16 producing plasmid and pTRE-Tight-Rluc8 reporter plasmid kept either in darkness (top) or illuminated with 740/25 nm light of 1 mW cm$^{-2}$ (bottom) for 48 h. (b) Rluc8 signals detected in dark-treated animals and in illuminated animals shown in (a) (n=3; error bars are s.e.m.). (c) Rluc8 signals in mice with subcutaneously injected HeLa cells co-transfected with pGAVPO plasmid encoding GAL4 (65)-VVD-VP16 and pU5-Rluc8 reporter plasmid kept in darkness (top) or illuminated with 470/15 nm light of 1 mW cm$^{-2}$ (bottom) for 48 h. (d) Rluc8 signals detected in the dark-treated and illuminated animals shown in (c) (n=3; error bars are s.e.m.). (e) Rluc8 signals detected in mice after hydrodynamic co-transfection with pKA-207I10 (encoding NLS-PpsR2-VP16-IRESv10-BphP1-mCherry-VP16) (50 µg) and pTRE-Tight-Rluc8 (5 µg) plasmids. Mice kept in darkness (top) or illuminated with 740/25 nm light of 5 mW cm$^{-2}$ (bottom) for 48 h. (f) Kinetics of the Rluc8 expression in mice shown in (e) kept in darkness or illuminated for 72 h (n=3; error bars are s.e.m.). (g) Rluc8 signals detected in mice after hydrodynamic co-transfection with pGAVPO (50 µg) and pU5-Rluc8 (5 µg) plasmids. Mice kept in darkness (top) or illuminated with 470/15 nm light of 5 mW cm$^{-2}$ (bottom) for 24 h. (h) Kinetics of Rluc8 expression in mice shown in (g) kept in darkness or illuminated for 72 h (n=3; error bars are s.e.m.).

Figure 14A:
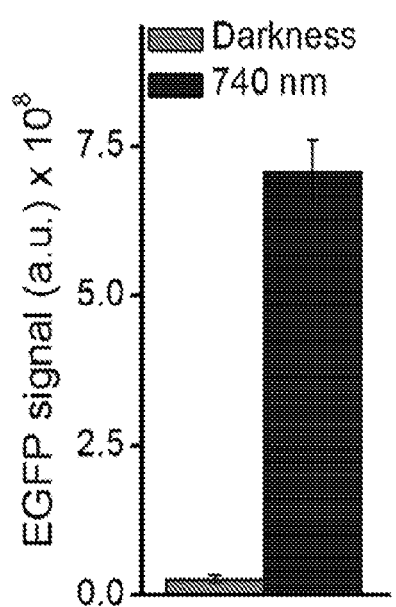
Figure 14B:
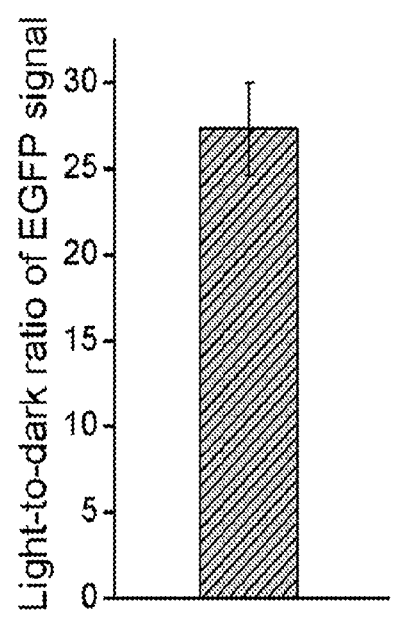

FIG. 14: Light-induced expression of EGFP from the pTRE-Tight-EGFP reporter plasmid. (a) Light-induced expression of EGFP from the pTRE-Tight-EGFP reporter plasmid. EGFP signal was detected in HeLa cells bearing BphP1-mCherry-TetR co-transfected with pCMV-104 and pTRE-Tight-EGFP plasmids. Cells were kept in darkness (gray) or under 740/25 nm light (dark red) for 48 h and analyzed using flow cytometry (n=5×10$^4$) (n=3, error bars are s.e.m.). (b) Light-to-dark ratio of the EGFP signals shown in (a).

Figure 15:
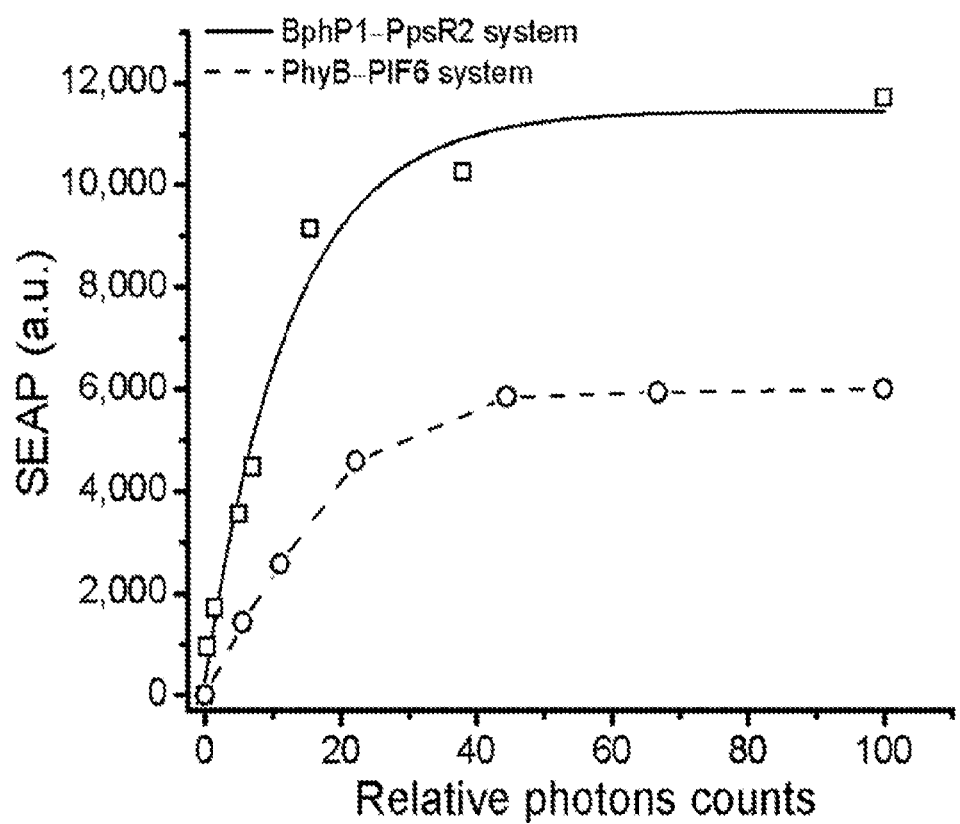

FIG. 15: Dose-response curves for light-induced SEAP expression for BphP1-PpsR2 and PhyB-PIF6 systems. SEAP signal was detected in HeLa cells with BphP1-mCherry-TetR, pTRE-Tight-SEAP and pCMV-104 plasmids (squares) and in HeLa cells with pTRE-Tight-SEAP plasmid and pKM022 plasmid (41), supplemented with 15 μM of phycocyanobilin (circles). Cells were kept in darkness or illuminated with 740/25 nm light for the BphP1-PpsR2 system or illuminated with 660/20 nm light in a case of the PhyB-PIF6 system.

FIG. 16a-16d: Comparison of penetration depth of far-red and NIR light in different mammalian tissues. Dependences of the photon counts at 660 nm (dashed line) and 740 nm (solid line) wavelengths on the depth of penetration for (a) mammalian brain, (b) breast, (c) muscle and (d) bone tissues.

Figure 16B:
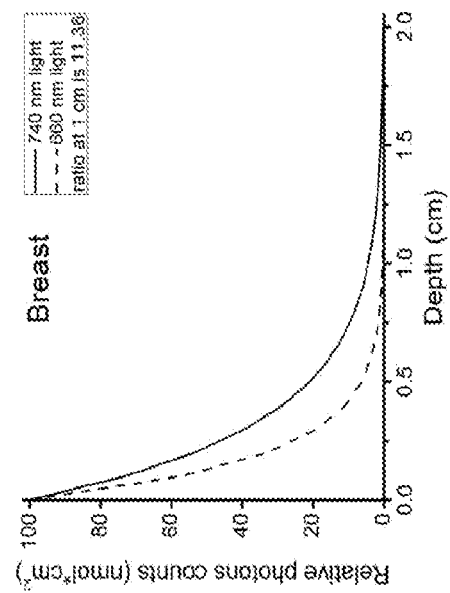
Figure 16D:
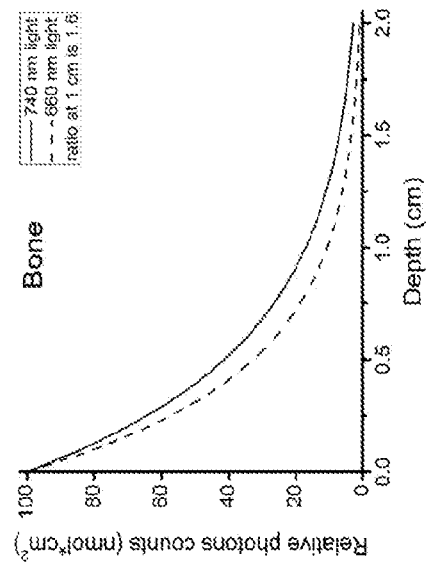
Figure 16A:
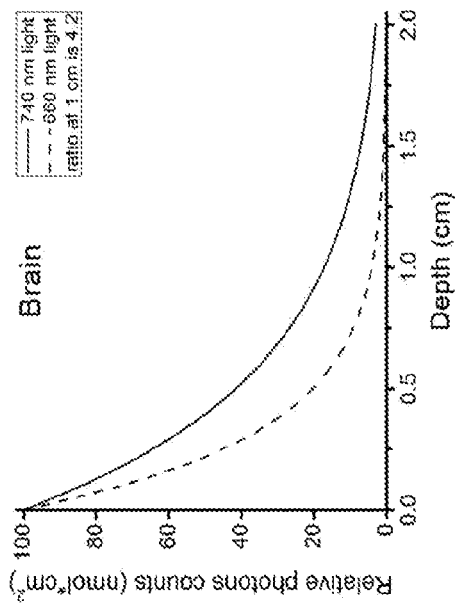
Figure 16C:
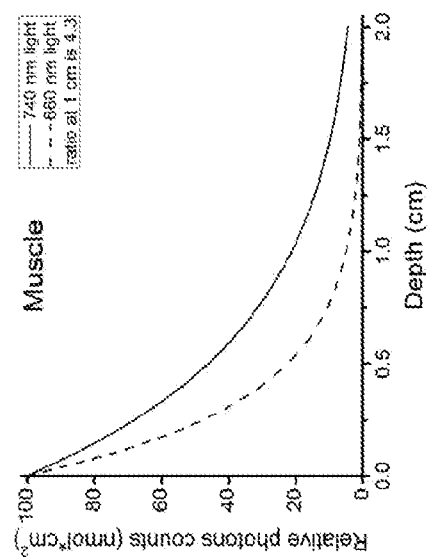
Figure 17:
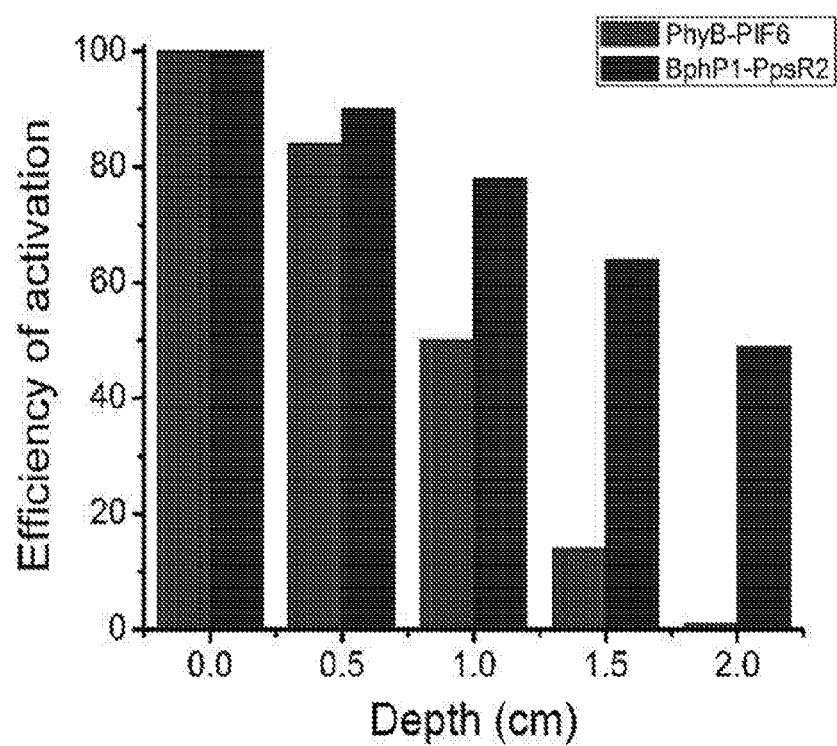

FIG. 17: Estimated efficiency of the SEAP light-induced expression for the BphP1-PpsR2 and PhyB-PIF6 systems at various depths in a muscle tissue. Dependence of the relative activation efficiency of the BphP1-PpsR2 and PhyB-PIF6 systems on the depth of a muscle tissue. The systems are activated with 740 nm (dark gray) and 660 nm (gray) light, respectively. Calculation of the relative efficiencies was based on the light-sensitivity measurements for both optogenetic systems (FIG. 15) and on the light-attenuation properties of a mammalian muscle tissue (FIG. 16c).

Figure 18:
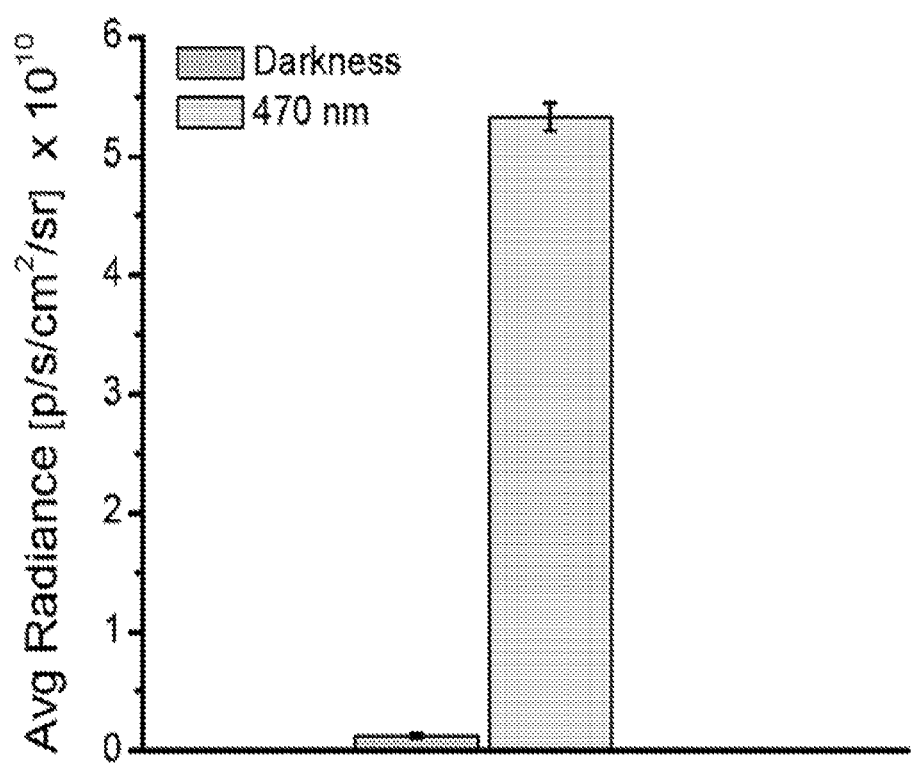

FIG. 18: Blue light-induced expression of Rluc8 in HeLa cells transfected with LightON system. The Rluc8 bioluminescence signal was detected in HeLa cells transiently transfected with the pGAVPO plasmid (42) and with the pU5-Rluc8 plasmid in a 1:1 ratio. 10 h after the transfection cells were continuosly illuminated with 470/15 nm light (1 mW cm$^{-2}$) or remained in darkness for 48 h (n=3, error bars are s.e.m.).

Figure 19:
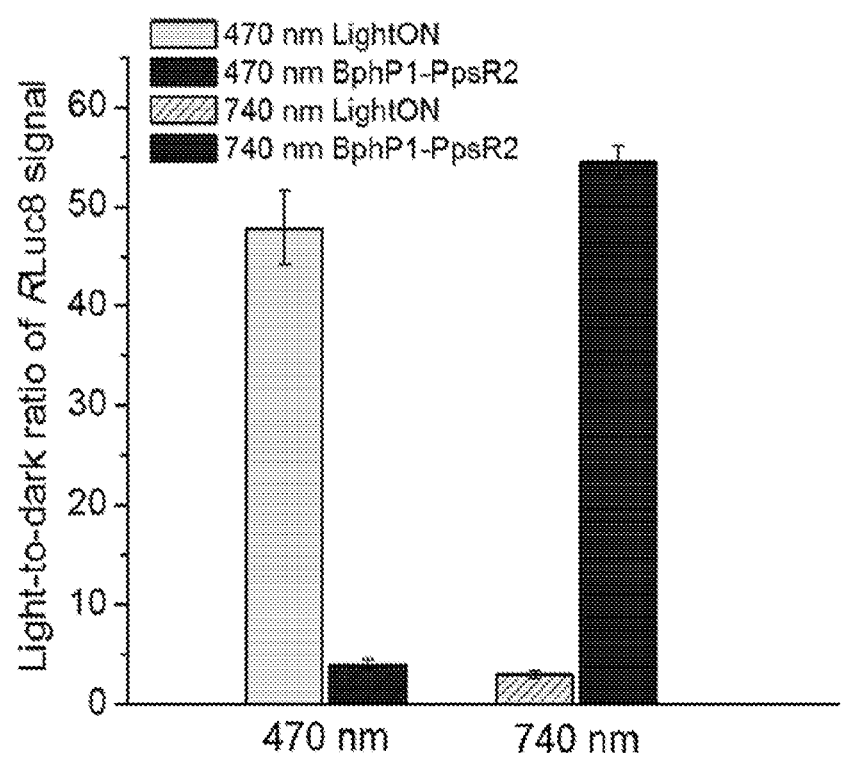

FIG. 19: Spectral compatibility of LightON and BphP1-PpsR2 systems. The light-to-dark ratio of Rluc8 bioluminescence signal detected in HeLa cells co-transfected with the pGAVPO plasmid$^3$ and with the pU5-Rluc8 plasmid in a 1:1 ratio (blue columns) and in HeLa cells expressing BphP1-mCherry-TetR co-transfected with the pTRE-Tight-Rluc8 and pCMV-104 plasmids with a 1:5 ratio (dark red columns). After the transfection, the cells were continuously illuminated for 48 h with either 470/15 nm (0.5 mW cm$^{-2}$) or 740/20 light (0.5 mW cm$^{-2}$) or remained in darkness (n=3, error bars are s.e.m.).

FIG. 20a-20c: Blue light-induced transcription activation in mice livers hydrodynamically transfected with high amounts of LightON plasmids. Rluc8 bioluminescence signals detected in mice after hydrodynamic co-transfection of the livers with the pGAVPO plasmid$^3$ (10 μg) and the pU5-Rluc8 reporter plasmid (300 μg). Mice kept (a) in darkness or (b) illuminated with 470/15 nm light of 5 mW cm$^{-2}$ for 24 h are shown. (c) The kinetics of the Rluc8 expression in mice kept in darkness or illuminated with 470/15 nm light at 5 mW cm$^{-2}$ continuously for 72 h is quantified (n=3; error bars are s.e.m.). The color bar in (a) and (b) indicates the total bioluminescence radiance in [photons s$^{-1}$ cm$^{-2}$ steradian$^{-1}$].

DETAILED DESCRIPTION OF THE INVENTION

Light-mediated control of protein-protein interactions to regulate metabolic pathways and gene expression is an important approach of optogenetics. Herein is disclosed the first optogenetic system based on a reversible light-induced binding of a bacterial phytochrome RpBphP1 and its natural partner RpPpsR2 (its Cys439Ser mutant is denoted as PpsR2 herein) from *Rhodopseudomonas palustris* bacteria. The BphP1-PpsR2 interaction is herein characterized extensively both in vitro and in live mammalian cells, and then used to translocate target proteins to specific cellular compartments, such as plasma membrane and nucleus. Using this approach, a light-control of cell morphology was achieved resulting in the substantial increase of cell area. Next, a light-induced gene expression was demonstrated with 40-fold contrast, and a Cre-mediated DNA recombination resulted in the 20-fold excess of positive cells. The unique characteristics of the BphP1-PpsR2 optogenetic system reported here are its sensitivity to 700-820 nm near-infrared light and its ability to utilize an endogenous biliverdin chromophore abundant in eukaryotes, including mammals and humans.

An isolated nucleic acid is provided encoding (i) a protein having the sequence of *Rhodopseudomonas palustris* BphP1 and (ii) a protein or peptide which is heterologous relative to *Rhodopseudomonas palustris*. In an embodiment, the nucleic acid is a cDNA.

Also provided is an isolated nucleic acid encoding (i) a protein having the sequence of *Rhodopseudomonas palustris* PpsR2 or a non-dimerizing variant thereof and (ii) a protein or peptide which is heterologous relative to *Rhodopseudomonas palustris*. In an embodiment, the nucleic acid is a cDNA.

Also provided is an isolated nucleic acid comprising a first and second portion, the first portion encoding a protein having the sequence of *Rhodopseudomonas palustris* BphP1 and a protein or peptide which is heterologous relative to *Rhodopseudomonas palustris*, and the second portion encoding a protein having the sequence of *Rhodopseudomonas palustris* PpsR2 or a non-dimerizing variant thereof and a protein or peptide which is heterologous relative to *Rhodopseudomonas palustris*.

In an embodiment, the first portion is contiguous with the second portion. In an embodiment, the first portion is contiguous with an oligonucleotide portion encoding a self-cleaving peptide, which oligonucleotide portion is contiguous with the second portion.

In an embodiment of the nucleic acids, the nucleic acid further encodes a detectable marker protein or detectable marker peptide. In an embodiment, the nucleic acid encodes a detectable marker protein which is a fluorescent protein.

A cell is provided, wherein the cell is not in a human being, transformed with the nucleic acid of as described herein.

A fusion protein is provided comprising a protein having the sequence of a *Rhodopseudomonas palustris* BphP1 and a second protein or peptide. A fusion protein is provided comprising a protein having the sequence of a *Rhodopseudomonas palustris* PpsR2 or a non-dimerizing variant thereof and a second protein or peptide. In an embodiment, the second protein or peptide is heterologous relative to *Rhodopseudomonas palustris*. In an embodiment, the fusion protein further comprises a detectable marker protein or detectable marker peptide. In an embodiment, the fusion protein comprises a detectable marker protein which is a fluorescent protein.

A method is provided for inducing interaction of a first protein with a second protein in a system, the method comprising
providing a system comprising (a) a fusion protein comprising (i) a protein having the sequence of a *Rhodopseudomonas palustris* BphP1 and (ii) the first protein, and (b) a fusion protein comprising (i) a protein having the sequence of a *Rhodopseudomonas palustris* PpsR2 or a non-dimerizing variant thereof and (ii) the second protein, and (c) an amount of biliverdin; and
irradiating the system with near infrared light sufficient to induce interaction of a *Rhodopseudomonas palustris* BphP1 with a *Rhodopseudomonas palustris* PpsR2 or a non-dimerizing variant thereof. In embodiments, the amount of biliverdin is present endogenously, added exogenously or produced enzymatically. An embodiment further comprises co-expression of heme oxygenase.

In an embodiment, the first or second protein is a DNA-binding protein. In an embodiment, the first or second protein comprises a transcriptional activator protein. In an embodiment, at least one fusion protein further comprises a detectable marker protein or detectable marker peptide. In an embodiment, the one fusion protein or both fusion proteins comprise different detectable marker proteins which are each fluorescent proteins. In an embodiment, the system is a eukaryotic cell. In an embodiment, the system comprises a plant, algae, fungi, yeast, insect, worm, avian, *xenopus*, fish or mammalian cell.

In an embodiment, the eukaryotic cell is in vivo. In an embodiment, the eukaryotic cell is in vivo.

In an embodiment, the method further comprises providing the system by transfecting the cell with a nucleic acid encoding the fusion protein comprising a protein having the sequence of a *Rhodopseudomonas palustris* BphP1.

In an embodiment, the method further comprises providing the system by transfecting the cell with a nucleic acid encoding the fusion protein comprising a protein having the sequence of a *Rhodopseudomonas palustris* PpsR2 or a non-dimerizing variant thereof and the second protein.

Also provided is a method for inducing translocation of a predetermined protein to a predetermined location in a cell comprising providing a system comprising (a) a fusion protein comprising (i) a protein having the sequence of a *Rhodopseudomonas palustris* BphP1 and (ii) a first protein, and (b) a fusion protein comprising (i) a protein having the sequence of a *Rhodopseudomonas palustris* PpsR2 or a non-dimerizing variant thereof and (ii) a second protein, and (c) an amount of biliverdin, wherein one of the first and second proteins is the predetermined protein and wherein the other of the first and second proteins is a protein that preferentially locates to the predetermined location in a cell; and
irradiating the system with near infrared light sufficient to induce interaction of a *Rhodopseudomonas palustris* BphP1 with a *Rhodopseudomonas palustris* PpsR2 or a non-dimerizing variant thereof.

In embodiments, the amount of biliverdin is present endogenously, added exogenously or produced enzymatically. An embodiment further comprises co-expression of heme oxygenase.

In an embodiment, the protein that preferentially locates to the predetermined location in a cell, preferentially locates to a plasma membrane of a cell.

In an embodiment, the protein that preferentially locates to the predetermined location in a cell, preferentially locates to an organelle of a cell.

In an embodiment, the protein that preferentially locates to the predetermined location in a cell, preferentially locates to a nucleus of a cell.

In an embodiment, the fusion protein comprising the first or second protein that preferentially locates to a nucleus, further comprises a DNA-binding protein.

In an embodiment, the fusion protein comprising the first or second protein that preferentially locates to a nucleus, further comprises a transcriptional activator protein.

In an embodiment, one fusion protein or both fusion proteins further comprise a detectable marker protein or detectable marker peptide.

In an embodiment, the one fusion protein or both fusion proteins comprises different detectable marker protein which are each fluorescent proteins.

In an embodiment of the methods, the cell is a eukaryotic cell. In an embodiment, the system comprises a plant, algae, fungi, yeast, insect, worm, avian, *xenopus*, fish or mammalian cell.

In an embodiment of the methods, the eukaryotic cell is in vivo. In an embodiment of the methods, the eukaryotic cell is in vitro.

In an embodiment, the method further comprises providing the system by transfecting the cell with a nucleic acid encoding the fusion protein comprising a protein having the sequence of a *Rhodopseudomonas palustris* BphP1.

In an embodiment, the method further comprises providing the system by transfecting the cell with a nucleic acid encoding the fusion protein comprising a protein having the sequence of a *Rhodopseudomonas palustris* PpsR2 or a non-dimerizing variant thereof.

In an embodiment, the near infra-red light is 700 nm to 820 nm light. In an embodiment, the near infra-red light is activating infra-red light.

In an embodiment, the methods further comprise irradiating the system with far infrared light sufficient to induce dissociation of a *Rhodopseudomonas palustris* BphP1 with a *Rhodopseudomonas palustris* PpsR2 or a non-dimerizing variant thereof. In an embodiment, further comprising irradiating the system with far infrared light sufficient to induce dissociation, the method subsequently reduces the interaction of a first protein with a second protein in the system. In an embodiment, further comprising irradiating the system with far infrared light sufficient to induce dissociation, the method subsequently induces relocation of a predetermined protein away from the predetermined location in a cell.

A kit is provided comprising any of the nucleic acid, fusion protein and/or system described herein and instructions for use.

In an embodiment, this invention also encompasses isolated non-naturally occurring nucleic acids encoding a non-canonical BphP having an HOS domain and/or a PpsR2 interacting counterpart. In an embodiment, this invention also encompasses a fusion protein comprising a non-canonical BphP having an HOS domain and/or a PpsR2 interacting counterpart. In an embodiment, this invention also encompasses methods comprising use of a non-canonical BphP having an HOS domain and/or a PpsR2 interacting counterpart. Non-canonical BphP and PpsR2 are found not only in the *Rhodopseudomonas palustris* but in several other bacteria. For example, *Bradyrhizobium* in which there are BphP and PpsR2 which also can interact with each other when irradiated with near infra-red light. Use of and non-naturally occurring compositions comprising these isolated protein pairs from an bacteria with high homology between RpBphP1 and BrBphP, as well as between RpPpsR2 and BrPpsR2, are encompassed. BrBphP and BrPpsR2 proteins are cloned from *Bradyrhizobium* strain ORS278, and their nucleotide and peptide sequences are publically available in the NCBI/NIH databases. The nucleic acids, fusion proteins and methods described herein are applicable mutatis mutandis to the non-canonical BphP and PpsR2 not present in *Rhodopseudomonas palustris*.

In an embodiment, the BphP1 has the sequence encoded by *Rhodopseudomonas palustris* gene rpa1537.

In an embodiment, the BphP1 has the sequence:

(SEQ ID NO: 1)
MVAGHASGSPAFGTADLSNCEREEIHLAGSIQPHGALLVVSEPDHRII

QASANAAEFLNLGSVLGVPLAEIDGDLLIKILPHLDPTAEGMPVAVRC

RIGNPSTEYDGLMHRPPEGGLIIELERAGPPIDLSGTLAPALERIRTA

GSLRALCDDTALLFQQCTGYDRVMVYRFDEQGHGEVFSERHVPGLESY

FGNRYPSSDIPQMARRLYERQRVRVLVDVSYQPVPLEPRLSPLTGRDL

DMSGCFLRSMSPIHLQYLKNMGVRATLVVSLVVGGKLWGLVACHHYLP

RFIHFELRAICELLAEAIATRITALESFAQSQSELFVQRLEQRMIEAI

TREGDWRAAIFDTSQSILQPLHADGCALVYEDQIRTIGDVPSTQDVRE

IAGWLDRQPRAAVTSTASLGLDVPELAHLTRMASGVVAAPISDHRGEF

LMWFRPERVHTVTWGGDPKKPFTMGDTPADLSPRRSFAKWHQVVEGTS

DPWTAADLAAARTIGQTVADIVLQFRAVRTLIAREQYEQFSSQVHASM

QPVLITDAEGRILLMNDSFRDMLPAGSPSAVHLDDLAGFFVESNDFLR

NVAELIDHGRGWRGEVLLRGAGNRPLPLAVRADPVTRTEDQSLGFVLI

FSDATDRRTADAARTRFQEGILASARPGVRLDSKSDLLHEKLLSALVE

NAQLAALEITYGVETGRIAELLEGVRQSMLRTAEVLGHLVQHAARTAG

SDSSSNGSQNKK.

In an embodiment, RpBphP1 has the nucleotide sequence:

(SEQ ID NO: 9)
atggtggcaggtcatgcctctggcagccccgcattcgggaccgccgat ctttcgaattgcgaacgtgaagagatccacctcgccggctcgatccag ccgcatggcgcgcttctggtcgtcagcgagccggatcatcgcatcatc caggccagcgccaacgccgcggaatttctgaatctcggaagcgtgctc ggcgttccgctcgccgagatcgacggcgatctgttgatcaagatcctg ccgcatctcgatcccaccgccgaaggcatgccggtcgcggtgcgctgc cggatcggcaatccctccacggagtacgacggtctgatgcatcggcct ccggaaggcgggctgatcatcgagctcgaacgtgccggcccgccgatc gatctgtccggcacgctggcgccggcgctggagcggatccgcacggcg ggctcgctgcgcgcgctgtgcgatgacaccgcgctgctgtttcagcag tgcaccggctacgaccgggtgatggtgtatcgcttcgacgagcagggc cacggcgaagtgttctccgagcgccacgtgcccgggctcgaatcctat ttcggcaaccgctatccgtcgtcggacattccgcagatggcgcggcgg ctgtacgagcggcagcgcgtccgcgtgctggtcgacgtcagctatcag ccggtgccgctggagccgcggctgtcgccgctgaccgggcgcgatctc gacatgtcgggctgcttcctgcgctcgatgtcgccgatccatctgcag tacctgaagaacatgggcgtgcgcgccaccctggtggtgtcgctggtg gtcggcggcaagctgtggggcctggttgcctgtcaccattatctgccg cgcttcatccatttcgagctgcgggcgatctgcgaactgctcgccgaa gcgatcgcgacgcggatcaccgcgcttgagagcttcgcgcagagccag tcggagctgttcgtgcagcggctcgaacagcgcatgatcgaagcgatc acccgtgaaggcgattggcgcgcagcgattttcgacaccagccaatcg atcctgcagccgctgcacgccgacggttgcgcgctggtgtacgaagac cagatcaggaccatcggtgacgtaccttccacgcaggatgttcgcgag atcgccgggtggctcgatcgccagccacgtgcggcggtgacctcgacc gcgtcgctcggtctcgacgtgccggagctcgcgcatctgacgcggatg gcgagcggcgtggtcgcggcgccgatttcggatcatcgcggcgagttt ctgatgtggttccgccccgagcgcgtccacaccgttacctgggcggc gatccgaagaagccgttcacgatgggcgatacaccggcggatctgtcg ccgcggcgctccttcgccaaatggcatcaggttgtcgaaggcacgtcc gatccgtggacggccgccgatctcgccgcggctcgcaccatcggtcag accgtcgccgacatcgtgctgcaattccgcgcggtgcggacactgatc gcccgcgaacagtacgaacagttttcgtcccaggtgcacgcttcgatg cagccggtgctgatcaccgacgccgaaggccgcatcctgctgatgaac gactcgttccgcgacatgttgccggcggggtcgccatccgccgtccat ctcgacgatctcgccgggttcttcgtcgaatcgaacgatttcctgcgc aacgtcgccgaactgatcgatcacggccgcgggtggcgcggcgaagtt ctgctgcgcggcgcaggtaatcgcccgttgccgctggcagtgcgcgcc gatccggtgacgcgcacggaggaccagtcgctcggcttcgtgctgatc ttcagcgacgctaccgatcgtcgcaccgcagatgccgcacgcacgcgt ttccaggaaggcattcttgccagcgcacgtcccggcgtgcggctcgac tccaagtccgacctcttgcacgagaagctgctgtccgcgctggtcgag aacgcgcagcttgccgcattggaaattacttacggcgtcgagaccgga cgcatcgccgagctgctcgaaggcgttcgccagtcgatgctgcgcacc gccgaagtgctcggccatctggtgcagcacgcggcgcgcacggccggc agcgacagctcgagcaatggctcgcagaacaagaag.

In an embodiment, the PpsR2 has the sequence encoded by the *Rhodopseudomonas palustris* gene ppsR2.

In an embodiment, the PpsR2 has the sequence:

(SEQ ID NO: 10)
gtggcgtcaaagtccgttcatgccgacatcacccttctgctcgatatg gagggtgtgattcgcgaagccaccctgtctccgacgatggcggccgag agcgtggacggttggctggggcgtcgctggagcgacatcgccggcgcc gaaggcggcgacaaggttcgccgcatggtcgaagacgccgccgcagc ggcatctcggctttccgccagatcaatcagcctttcccgagcggcgtc -continued

```
gaaatcccgatcgaattcaccacgatgctgctgggcgaccgcaccggc
atgatcgcggtcggcaagaacatgcaggcggtcaccgagctgcattcc
cggctgatcgctgcgcagcaggcgatggagcgcgactattggcggttg
cgtgaattggagactcgctaccgcctggtgttcgacgctgccgccgat
gcggtgatgatcgtctccgccggcgacatgcgcatcgtcgaagccaac
cgggcggcggtgaatgcgatcagccgtcgagcgcggcaatgacgac
cttgcggggcgtgatttcctcgccgaagtggcggctgccgatcgcgat
gcggtgcgcgacatgctggcccaggtgcgtcagcgcggcaccgcactc
agcgtcctcgttcatctcggccgttacgaccgcgcctggatgctgcgc
ggttcgctgatgtcgtccgagcgtcgtcaggttttcctgctgcacttc
accccggtgaccacgactcccgcgatcgacgacgtcgacgatgatgcc
gtgctgcgcgggctgatcgatcgcattcccgacgggttcgtcgcactg
gattcggaaggcgtcgttcgtcacgccaaccaggcgtttctcgatctg
gtccagatcggctccaagcctgcggcggtcggacgatcgctgggcgtc
tggatgggtcgtccgggcgccgatctgtccagcttgctgacgctgctg
cggcgctacaagacggtgcggctgttccaaacgacgatccgcggcgag
ctcggcaccgagactgaagtcgaggtctcggccgtcgacggcgaggac
gaccaatacatcggcgttctgatgcgcaatgtcgcgcgacgcctcgac
gctgcggacgaccacgatgccttgcgtcaggcgctcggcccgatcagc
aagcagctcgggcgatcctcgctgcgcaagctggtgaagaacgccgtg
agcattgtcgagcagcactacgtgaaggaagcgctgttgcgatccaag
ggcaatcgcacggcaactgccgaactgctcggattgagccggcagagc
ctttatgcaaaactcaacagctacggcttcgacgacaaaggtgtcgtt
gcttctgctgccgacggtgcagagggcgcctcagacgacgcagaggat.
```

In an embodiment, the RpPpsR2 has the sequence:

(SEQ ID NO: 2)
MASKSVHADITLLLDMEGVIREATLSPTMAAESVDGWLGRRWSDIAGA

EGGDKVRRMVEDARRSGISAFRQINQPFPSGVEIPIEFTTMLLGDRTG

MIAVGKNMQAVTELHSRLIAAQQAMERDYWRLRELETRYRLVFDAAAD

AVMIVSAGDMRIVEANRAAVNAISRVERGNDDLAGRDFLAEVAAADRD

AVRDMLAQVRQRGTALSVLVHLGRYDRAWMLRGSLMSSERRQVFLLHF

TPVTTTPAIDDVDDDAVLRGLIDRIPDGFVALDSEGVVRHANQAFLDL

VQIGSKPAAVGRSLGVWMGRPGADLSSLLTLLRRYKTVRLFQTTIRGE

LGTETEVEVSAVDGEDDQVIGVLMRNVARRLDAADDHDALRQALGPIS

KQLGRSSLRKLVKNAVSIVEQHYVKEALLRSKGNRTATAELLGLSRQS

LYAKLNSYGFDDKGVVASAADGAEGASDDAED.

In an embodiment, the PpsR2 has the non-dimerizing variant sequence:

(SEQ ID NO: 3)
MASKSVHADITLLLDMEGVIREATLSPTMAAESVDGWLGRRWSDIAGA

EGGDKVRRMVEDARRSGISAFRQINQPFPSGVEIPIEFTTMLLGDRTG

MIAVGKNMQAVTELHSRLIAAQQAMERDYWRLRELETRYRLVFDAAAD

AVMIVSAGDMRIVEANRAAVNAISRVERGNDDLAGRDFLAEVAAADRD

AVRDMLAQVRQRGTALSVLVHLGRYDRAWMLRGSLMSSERRQVFLLHF

TPVTTTPAIDDVDDDAVLRGLIDRIPDGFVALDSEGVVRHANQAFLDL

VQIGSKPAAVGRSLGVWMGRPGADLSSLLTLLRRYKTVRLFQTTIRGE

LGTETEVEVSAVDGEDDQVIGVLMRNVARRLDAADDHDALRQALGPIS

KQLGRSSLRKLVKNAVSIVEQHYVKEALLRSKGNRTATAELLGLSRQS

LYAKLNCYGFDDKGVVASAADGAEGASDDAED.

Also provided is a method for artificially expressing a heterogenous gene in vivo in a subject comprising administering to the subject: (a) a nucleic acid encoding (i) a protein having the sequence of a *Rhodopseudomonas palustris* BphP1 and (ii) a TetR tetracycline repressor protein (TetR) or a VP16 transcriptional activation domain (VP16); (b) a nucleic acid encoding (i) nuclear localization signal, a protein having the sequence of a *Rhodopseudomonas palustris* PpsR2 or a non-dimerizing variant thereof and (iii) a VP16 or a TetR; and (c) a nucleic acid encoding (i) a tetracycline response element (TRE) and the heterogenous gene;

wherein only one of (a) and (b) encodes a VP16 and the other of (a) or (b) encodes a TetR; and irradiating the system with near infrared light sufficient to induce interaction of a *Rhodopseudomonas palustris* BphP1 with a *Rhodopseudomonas palustris* PpsR2 or a non-dimerizing variant thereof and thereby effect expression of the heterogenous gene.

In an embodiment, the method further comprises administering an amount of biliverdin to the subject.

In an embodiment, the method further comprises detecting the expression of the heterogenous gene in the subject.

In an embodiment, the method further comprises quantifying the expression of the heterogenous gene in the subject.

In an embodiment, the method further comprises administering to the subject a blue light-activated gene expression system for a second heterogeneous gene and irradiating the system with blue light sufficient to induce expression of the second heterogenous gene.

An exemplary blue light-activated gene expression system is that described in Wang et al., *Nature Methods*, 9(3):266-269, which is hereby incorporated by reference in its entirety. In an embodiment, the system is irradiated with blue light comprising 470 nm light.

In an embodiment, the TRE is comprises a pTRE plasmid.

Optionally, the activation domain of the methods and constructs described herein may be replaced with an alternative activation domain such as a p65 activation domain (GAVP) (See Wang et al., *Nature Methods*, 9(3):266-269).

In an embodiment of the methods, the method is performed on a eukaryotic cell. In an embodiment of the methods reciting a eukaryotic cell, the cell is in a human. In an embodiment of the methods reciting a eukaryotic cell, the cell is not in a human. In an embodiment of the methods reciting a eukaryotic cell, the cell is in a mammalian cell or mammalian-derived cell.

All combinations of the various elements described herein are within the scope of the invention unless otherwise indicated herein or otherwise clearly contradicted by context.

This invention will be better understood from the Experimental Results, which follow. However, one skilled in the art will readily appreciate that the specific methods and results discussed are merely illustrative of the invention as described more fully in the claims that follow thereafter.

Experimental Results

Introduction

A non-canonical bathy bacterial phytochrome RpBphP1 (BphP1) from purple photosynthetic bacteria *Rhodopseudomonas palustris* may perform its signaling function by interacting with a transcriptional repressor RpPpsR2 when illuminated with NIR light (22). The effector module of BphP1 consists of two domains, PAS/PAC (PAS domain with additional C-terminal residues) and HOS (2-helix output sensor), with no detectable enzymatic activity. Recently, a BphP1-RpPpsR2 heterodimerization was observed in the NIR-illuminated BphP1 and RpPpsR2 protein mixture using gel filtration; however, no further characterization of this interaction was performed (23), and whether it is a practically usable interaction is unknown.

Examples

Figure 6A:
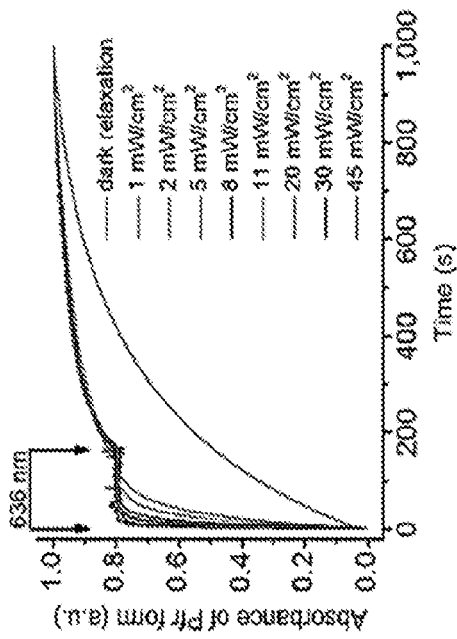
FIG. 6(a)-6(b): Kinetics of BphP1 photoconversion in vitro. (a) Dependence of the Pfr→Pr photoconversion on the 740/25 nm light intensity. The gradual increase in absorbance of the Pr state was observed for all tested light intensities. Kinetic curves can be fitted with monoexponential functions ($R^2 \geq 0.958$ for all curves). (b) Dependence of the Pr→Pfr photoconversion on the 636/20 nm light intensity. The achievable with 636 nm light 0.8 value of the Pfr ground state is likely represents an equilibrium between the Pfr and Pr states because 636/20 light is also absorbed by the Pfr state, thus causing its partial photoconversion back to the Pr state.
Figure 6B:
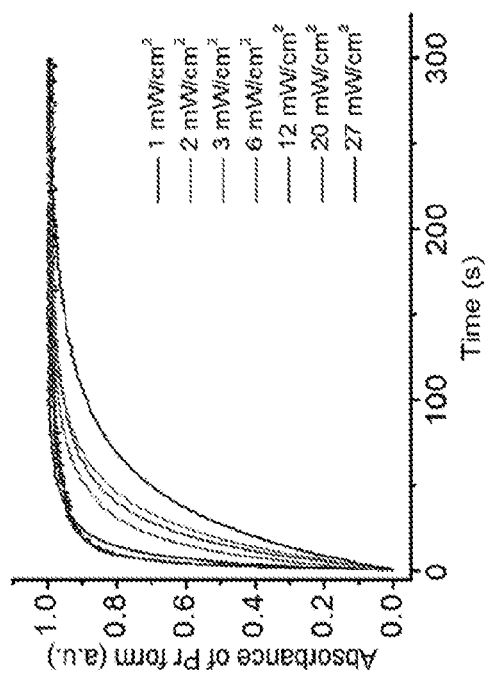

Properties of purified BphP1. In its ground Pfr state, BphP1 absorbs maximally at 412 nm (Soret band) and at 756 nm (Q band) (FIG. 1a). Upon NIR illumination, it photoconverts into the Pr state with absorbance at 390 nm and 678 nm for Soret and Q bands, respectively. A 4.3-fold decrease in absorbance at 756 nm upon 740/25 nm irradiation was observed (Table 1). The highest light sensitivity of the Pfr state was observed at ~740-780 nm, with notable BphP1 photoconversion at 800 nm (FIG. 1b). Kinetics of the Pfr→Pr photoconversion was monoexponential (FIG. 6a). The half-time of the Pfr→Pr transition was 28 s at 1 mW cm$^{-2}$ and decreased to 3.5 s at 27 mW cm$^{-2}$ (FIG. 1c). After the Pfr→Pr photoconversion, BphP1 returned to the ground state in darkness with a half-time of 170 s. BphP1 could undergo repeated cycles of Pfr→Pr photoconversion followed by dark relaxation back to the Pfr state (FIG. 1d). Irradiation with 636 nm light restored Pfr absorbance to ~80% (FIG. 1a). The remaining ~20% were restored during dark relaxation (FIG. 6b). The half-time of the Pr→Pfr conversion depended on the 636 nm light intensity, ranging from 21 s at 1 mW cm$^{-2}$ to 3.0 s at 45 mW cm$^{-2}$ (FIG. 1e). Multiple cycles of photoswitching did not lead to notable changes in absorbance (FIG. 1f).

Figure 7A:
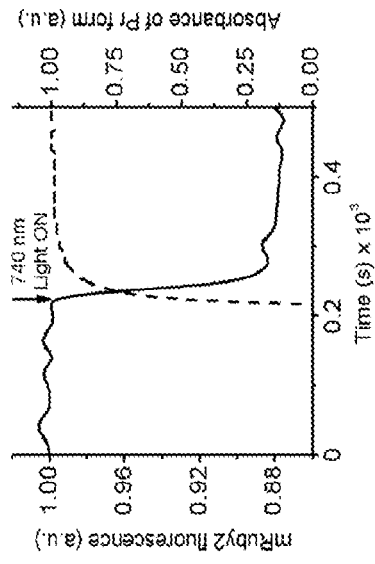
FIG. 7(a)-7(c): FRET-based approach for characterization of BphP1-PpsR2 interaction. (a) Overlap of the emission spectrum of mRuby2 (dashed lines) and absorbance spectrum of BphP1 in the Pr state. (b) Changes of FRET (solid line) during Pfr→Pr photoconversion of BphP1-mRuby2 (dashed line). (c) Dependence of the FRET changes on power of 740/25 nm illumination of the PpsR2-mRuby2 and BphP1 mixture.
Figure 7B:
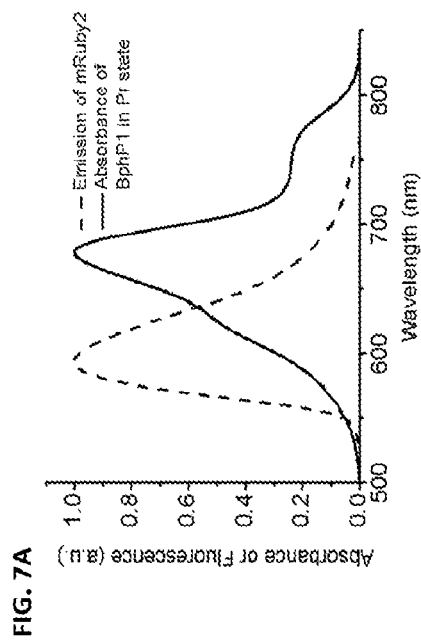
Figure 7C:
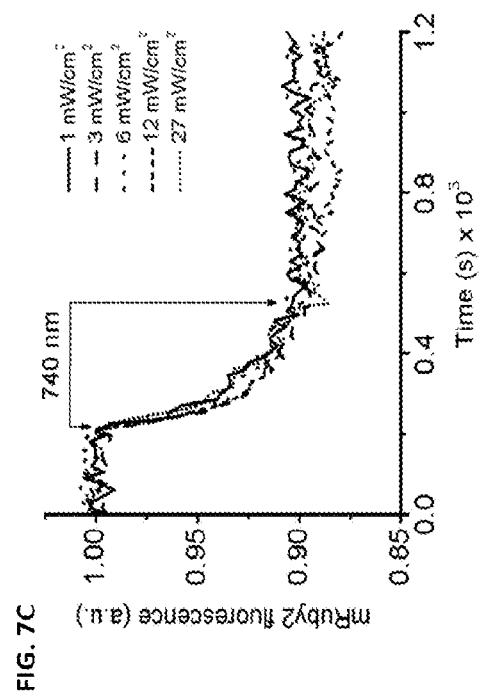

BphP1-PpsR2 interaction in vitro. RpPpsR2 has a single cysteine residue in position 439 and forms a noncovalent homodimer. To exclude the possibility of disulfide bond formation, cysteine 439 was substituted with serine and named this RpPpsR2/C439S variant PpsR2. mRuby2 was then fused to the C-terminus of PpsR2 and the BphP1-PpsR2 interaction characterized using FRET. mRuby2 emission and BphP1 absorbance in the Pr state have good spectral overlap (FIG. 7a), resulting in quenching of mRuby2 fluorescence (FIG. 7b). 740 nm light caused an increase in the Pr state, and up to 12% decrease in mRuby2 fluorescence resulted from the BphP1-PpsR2-mRuby2 binding. A 27-fold change in 740 nm light intensity did not cause changes in the kinetics of the mRuby2 fluorescence decrease (FIG. 7c). For all intensities tested, the fluorescence quenching exhibited a half-time of ~60 s, which was larger than observed for BphP1 alone (FIG. 1c). This suggested that PpsR2 did not bind BphP1 in the Pfr state, and that the BphP1-PpsR2 interaction was not limited by the rate of Pfr→Pr photoconversion but rather by BphP1 and/or PpsR2 structural changes involved in the interaction.

Using 740 nm for the Pfr→Pr and 636 nm for the Pr→Pfr photoconversion, several cycles of FRET changes (FIG. 1g) were monitored with half-times of ~60 s and ~30 s, respectively (Table 1). The observed incomplete Pr→Pfr switching with 636 nm light possibly was caused by overlap of the Pr and Pfr spectra at this wavelength (FIG. 1a). Dark relaxation in the BphP1-PpsR2 complex was slower than photoswitching with 636 nm and depended on the BphP1:PpsR2 ratio, with shorter half-times of Pr→Pfr dark relaxation (as detected by Pfr absorbance) corresponding to the larger BphP1 concentrations (FIG. 1h). The dark relaxation half-time was 900 s (Table 1), suggesting that the PpsR2 binding to BphP1 substantially slowed the Pr→Pfr relaxation and BphP1-PpsR2 dissociation in darkness. After complete dark relaxation the complexes can be formed again by 740 nm light illuminating (FIG. 1i).

TABLE 1

Characteristics of BphP1 and its interaction with PpsR2 in vitro.

| Proteins | Chromophore state | Absorbance maximum, nm | Extinction coefficient[1], $M^{-1}cm^{-1}$ | Absorbance change upon photoconversion, fold[2] | | Half-time (s) of[3] | |
|---|---|---|---|---|---|---|---|
| | | | | at 756 nm | at 678 nm | photoconversion | dark relaxation |
| BphP1 | Pr | 678 | 87,500 | 4.3 (7.0) | 0.48 (0.45) | 16 (Pr→Pfr, with 636/20 nm) | 210 |
| BphP1 and PpsR2 | | | | | | 30 (Pr→Pfr, with 636/20 nm) | 900 |
| BphP1 | Pfr | 756 | 78,300 | | | 19 (Pfr→Pr, with 740/25 nm) | N.A. |
| BphP1 and PpsR2 | | | | | | 60 (Pfr→Pr, with 740/25 nm) | |

[1]Calculated based on an extinction coefficient of BV, as described[1];
[2]Measured after irradiation either by a 740/25 nm LED array or by a 785/2 nm laser diode (in parenthesis);
[3]BphP1:PpsR2 molar ratio of 8:1 and photoconversion light intensity of 2 mW cm$^{-2}$ were used.
N.A., not applicable.

Figure 2A:
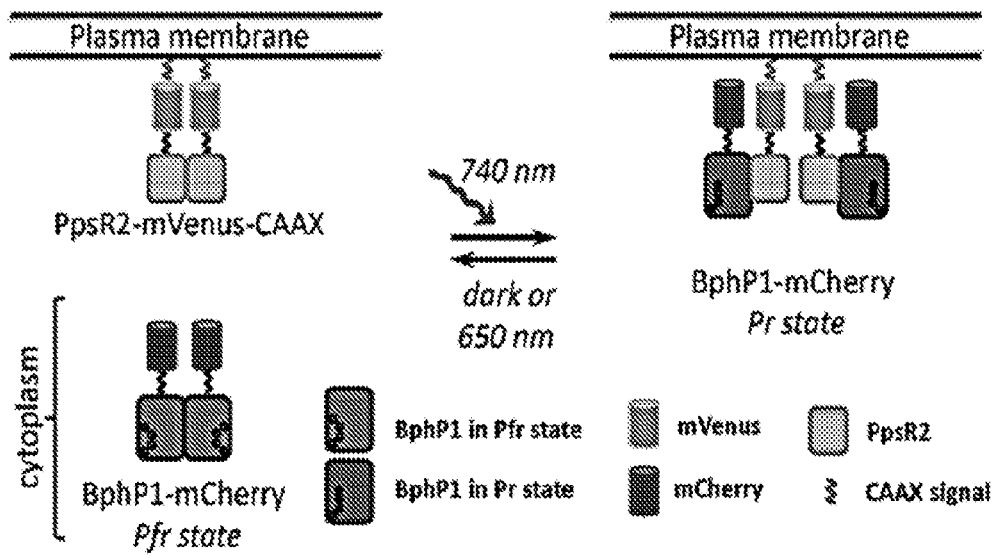
FIG. 2a-2f: Light-induced re-localization of BphP1 to the plasma membrane. (a) A model for the light-induced interaction between cytoplasmic BphP1-mCherry and membrane-bound PpsR2-mVenus-CAAX. (b) Fluorescence images of a HeLa cell co-expressing PpsR2-mVenus-CAAX (green) and BphP1-mCherry (red) before illumination (left), after 3 min of 740/40 nm illumination with 0.9 mW cm$^{-2}$ (middle), and after 20 min of dark relaxation (right). Bars, 10 μm. (c) Intensity profile of BphP1-mCherry fluorescence of the cell in (b) marked with a white line before (solid line) and after (dashed line) 3 min of 740/40 nm illumination. (d) Intensity profile of BphP1-mCherry fluorescence of the cell in (b) marked with a white line after 3 min of 740/40 nm illumination (dashed line) and after subsequent 24 min in darkness (dotted line). (e) Time-course of BphP1-mCherry fluorescence intensity in the cytoplasm during three cycles of 3 min of 740/40 nm irradiation with 0.2 mW cm$^{-2}$ followed by 30 min in darkness (n=5; white lines represent mean±s.e.m.). mCherry fluorescence was measured every 15 s during 740/40 nm light illumination and every 180 s during dark relaxation. (0 Time-course of the BphP1-mCherry fluorescence intensity in the cytoplasm during three cycles of 3 min of 740/40 nm irradiation with 0.2 mW cm$^{-2}$ followed by 3 min of 650/10 nm irradiation with 0.35 mW cm$^{-2}$ (n=5; white lines represent mean±s.e.m.). mCherry fluorescence was measured every 15 s. All imaging was performed at 37° C. using an epifluorescence microscope. Light intensities were measured at the back focal plane of a 60×1.35 NA objective lens.
Figure 2B:
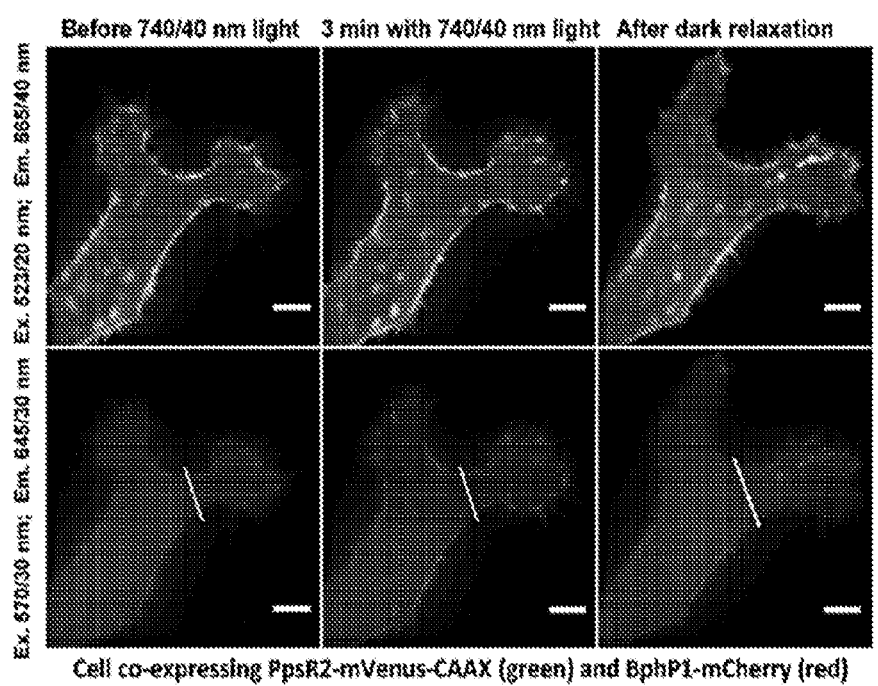
Figure 2C:
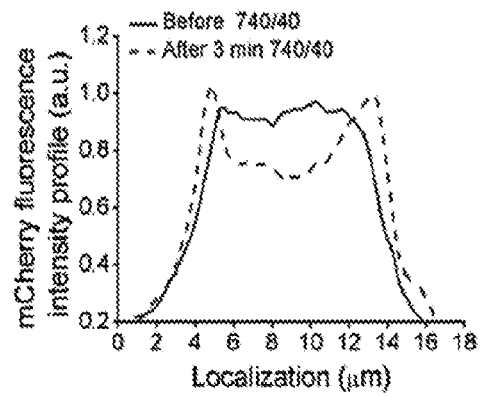
Figure 2D:
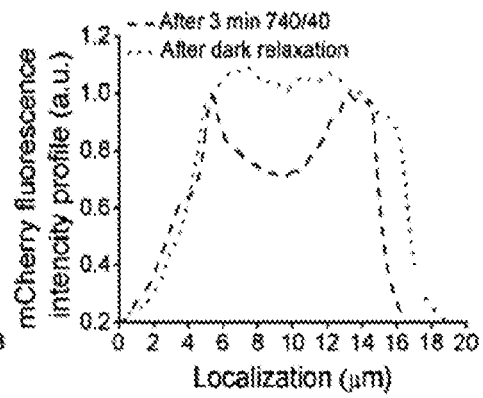
Figure 2E:
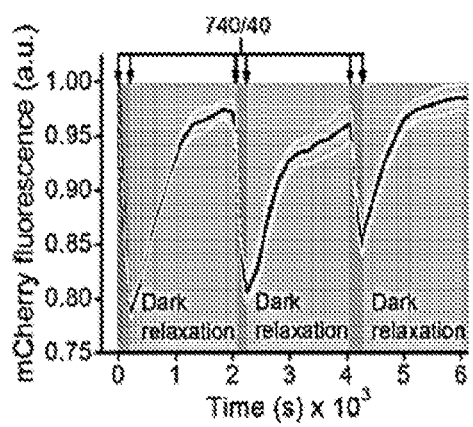
Figure 2F:
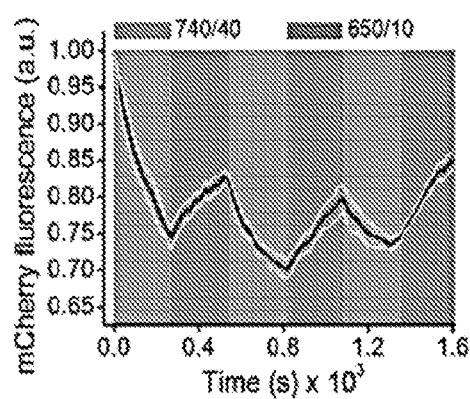
Figure 8:
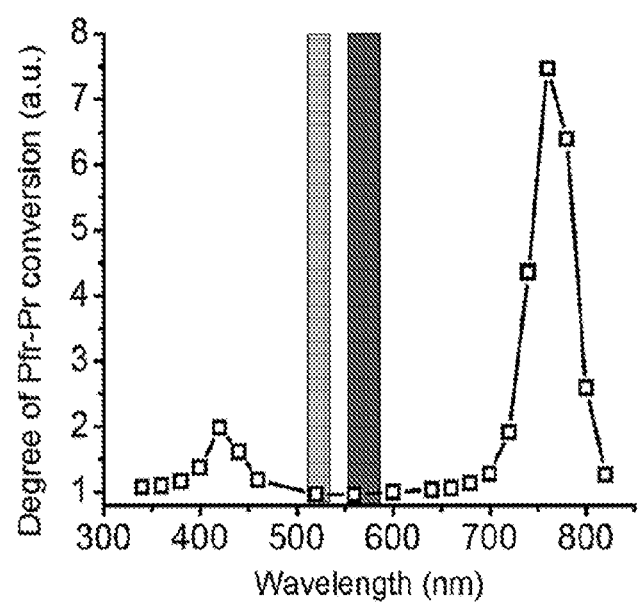
FIG. 8: Overlap of wavelengths used for mVenus and mCherry excitation with action spectrum of Pfr→Pr photoconversion. The lighter gray box outlines the wavelength range transmitted by 523/20 nm filter used for mVenus excitation, and the darker gray box outlines the wavelength range transmitted by 570/30 nm filter used for mCherry excitation. The action spectrum of the Pfr→Pr photoconversion was measured as the relative decrease of Pfr absorbance detected at 780 nm upon irradiation with light of specific wavelength (open squares).
Figure 9:
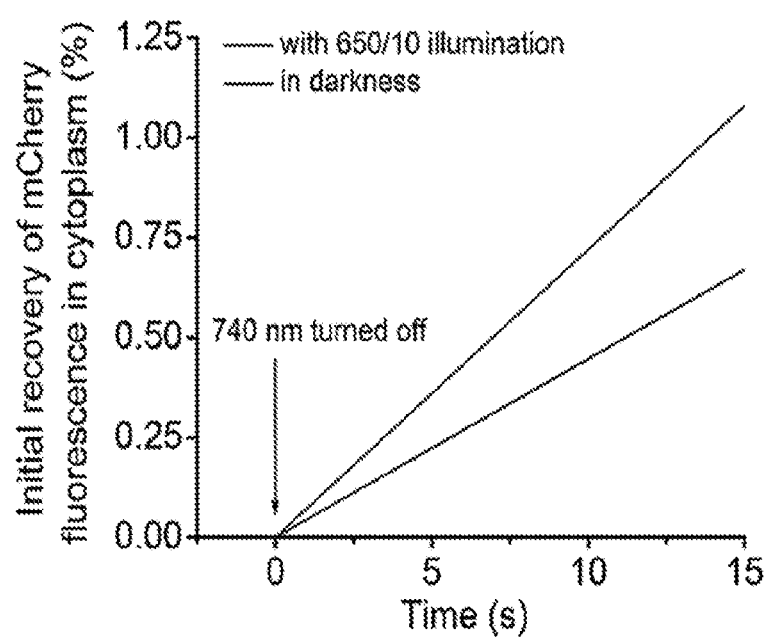
FIG. 9: Initial recovery of the mCherry cytoplasmic intensity under 650 nm light and in darkness. The linear fitting of the mean recovery kinetics of mCherry fluorescence in cytoplasm of cells right after 740/40 nm illumination either in darkness (black line; n=5) or after turning on 650/10 nm light (red line; n=5). The HeLa cells were co-expressing BphP1-mCherry and PpsR2-mVenus-CAAX constructs. The tangent of the angles that correspond to the initial mCherry recovery rates, are 0.044% s-1 and 0.072% s-1, respectively.

BphP1-PpsR2 interaction in mammalian cells. To study the BphP1-PpsR2 interaction in mammalian cells a translocation assay was used (FIG. 2a). PpsR2 was fused with mVenus and a -CAAX plasma membrane localization signal, and BphP1 with mCherry for cytoplasmic expression. Excitation of these fluorescent proteins did not photoconvert BphP1 (FIG. 8). Illumination of HeLa cells with 740 nm light caused the translocation of BphP1-mCherry to the plasma membrane and a 25% decrease in mCherry cytoplasmic intensity after 3 min of 740 nm illumination detected with epifluorescence microscope (FIG. 2b,c). Subsequent dark incubation restored BphP1-mCherry fluorescence in the cytoplasm to the original level in ~24 min (FIG. 2b,d). The reversibility of the BphP1 translocation to the plasma membrane and back to the cytoplasm was demonstrated for 3 cycles of 3 min of 740 nm illumination followed by 30 min of dark relaxation (FIG. 2e), with the recovery of ~95% of the initial mCherry cytoplasmic intensity. Then effect of 650 nm light was studied on acceleration of the BphP1 dissociation from the plasma membrane and found a 1.6-fold higher initial rate of BphP1-mCherry cytoplasmic signal recovery as compared to that in darkness (FIG. 9). However, complete dissociation of the BphP1-PpsR2 complexes required darkness. Illumination with 740 nm and 650 nm light for 3 min each resulted in ~8% reversible changes of the BphP1-mCherry cytoplasmic signal after the initial 25% decrease (FIG. 20, indicating that one third of the BphP1-PpsR2 complexes could be modulated with light.

Figure 3A:
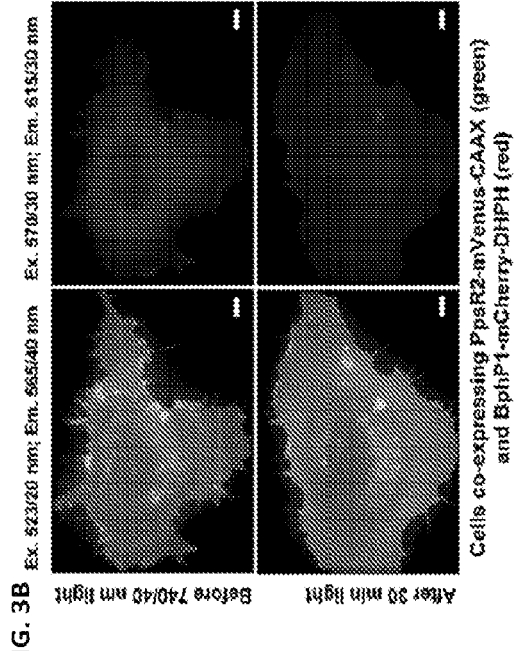
FIG. 3a-3d: Light-induction of cellular cytoskeletal rearrangements. (a) A model for the light-induced recruitment of cytoplasmic BphP1-mCherry-DHPH to membrane-bound PpsR2-mVenus-CAAX that results in cytoskeletal rearrangements of mammalian cells. (b, c) Fluorescence images of HeLa cells co-expressing either (b) BphP1-mCherry-DHPH (red) and PpsR2-mVenus-CAAX (green) or (c) BphP1-mCherry-DHPH (red) and mVenus-CAAX control (green) before (top) and after (bottom) 30 min irradiation with 740/40 nm light of 0.2 mW cm$^{-2}$ (first 3 min continuous irradiation with 740/40 nm followed by 27 min of pulse illumination 15 s On 45 s Off). Bars, 10 μm. (d) Time dependent size changes of HeLa cells, which co-express either BphP1-mCherry-DHPH and PpsR2-mVenus-CAAX (n=5; error bars are s.e.m.), or BphP1-mCherry-DHPH and mVenus-CAAX control (n=5; error bars are s.e.m.), during irradiation with 740/40 nm light of 0.2 mW cm$^{-2}$ (first 3 min continuous irradiation with 740/40 nm followed by 27 min of pulsed illumination 15 s On and 45 s Off). Fluorescent images were taken every 15 s during continuous and every 60 s during pulsed irradiation with 740/40 nm. All imaging was performed at 37° C. using an epifluorescence microscope. The light power densities were measured at the back focal plane of a 60×1.35 NA objective lens.
Figure 3C:
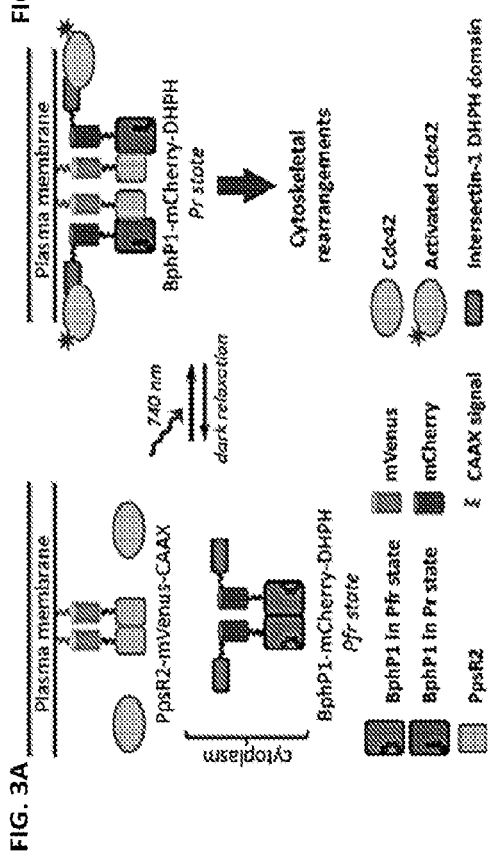
Figure 3B:
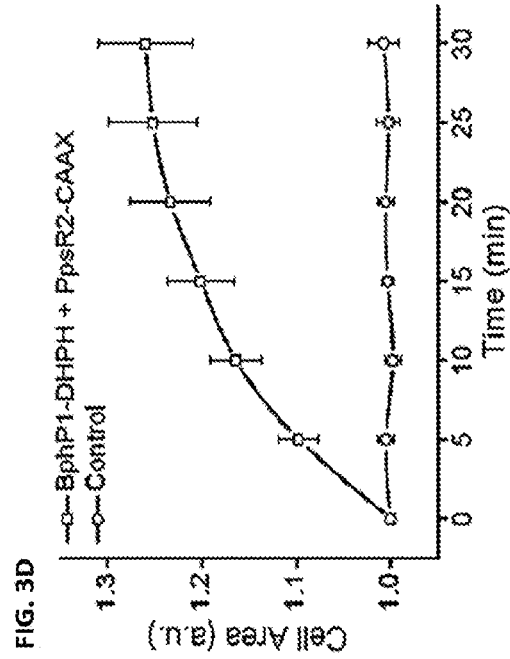
Figure 3D:
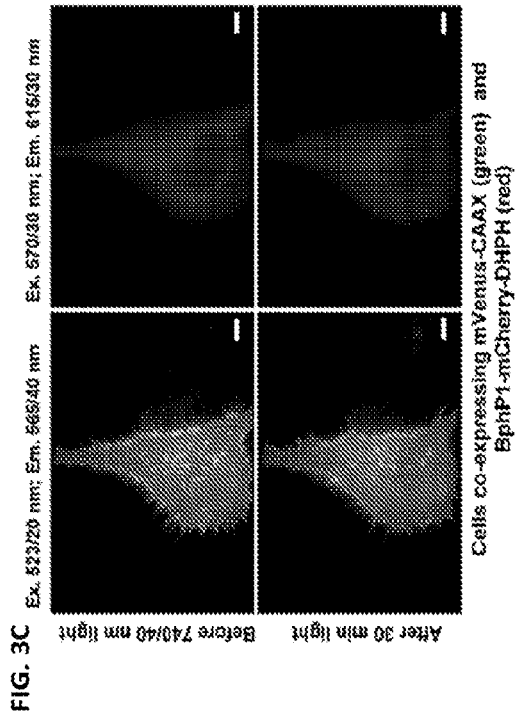
Figure 10:
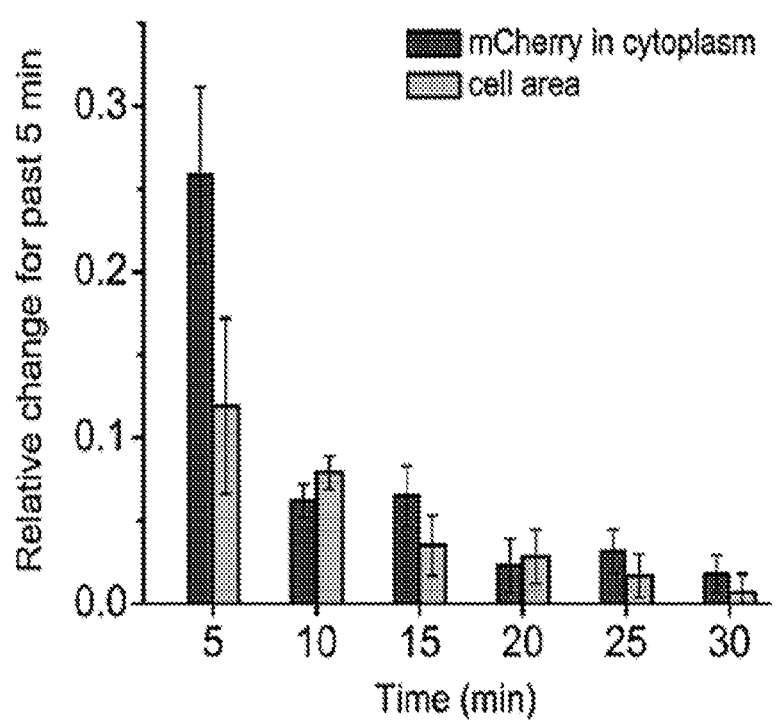
FIG. 10: The relative decrease in mCherry cytoplasmic fluorescence and relative increase in cell area in 5 min periods from the beginning of cell illumination with 740/40 nm. The HeLa cells co-expressed the BphP1-mCherry-DHPH and PpsR2-mVenus-CAAX constructs (n=5, error bars are s.e.m.). The initial (during the first 5 min) relative decrease in the BphP1-mCherry-DHPH in cytoplasm was more than 2-fold larger than that of the increase in the cell area. No substantial difference between these two characteristics was observed in the later time periods.

Light-induced activation of a signaling pathway. The BphP1-PpsR2 interaction was next utilized for the recruitment of a DHPH domain of intersectin-1 (ref 43) to the plasma membrane for activation of the small GTPase Cdc42 (ref 44, 45). The DHPH domain was fused to the C-terminus of BphP1-mCherry and co-expressed the construct in HeLa cells with PpsR2-mVenus-CAAX (FIG. 3a). 740 nm illumination caused changes of cell morphology and a gradual increase of the cell area with a plateau after ~30 min (FIG. 3b). No notable changes were detected in cells co-transfected with BphP1-mCherry-DHPH and mVenus-CAAX (FIG. 3c). In the former experiment, the area increase reached 50% in some cells, with an average increase of ~25% (FIG. 3d). The initial relative decrease of BphP1-mCherry-DHPH in the cytoplasm was 2-fold higher than the cell area increase, indicating that BphP1-mCherry-DHPH translocated mainly during the first 5 min of 740 nm irradiation. Further changes were rather similar for mCherry fluorescence and cell area, suggesting that they were caused by an increase in the cell area (FIG. 10).

Figure 11:
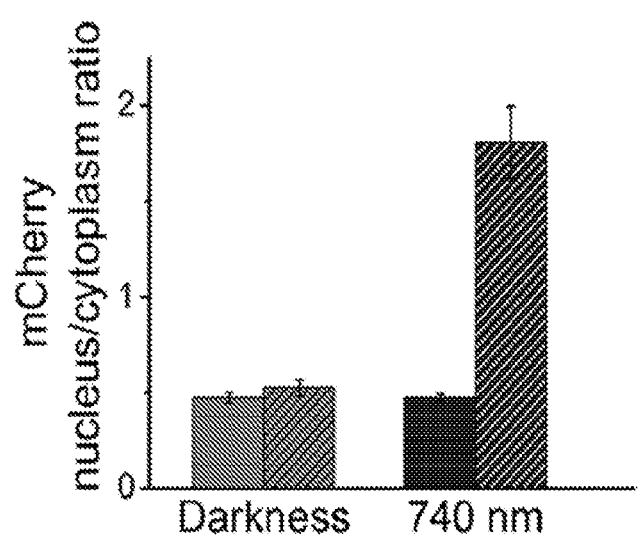
FIG. 11: Analysis of light-induced recruitment of BphP1-mCherry to nucleus. mCherry nucleus-to-cytoplasm intensity ratio in HeLa cells stably expressing BphP1-mCherry transfected with pCMV-160 (dashed bars) or not transfected (solid bars). Cells were kept in darkness or irradiated with 740/25 nm light (30 s On, 180 s Off) of 1 mW cm-2 for 24 h (n=20, error bars are s.e.m.). Cell imaging was performed using an epifluorescence microscope at 37° C.

BphP1 recruitment to the cell nucleus. To examine whether optogenetically induced nuclear import could be achieved, HeLa cells that stably expressed BphP1-mCherry were transfected with PpsR2-mVenus containing a nuclear localization signal (NLS). In darkness NLS-PpsR2-mVenus localized to the nucleus, and BphP1-mCherry stayed in the cytoplasm (FIG. 4a), with a mCherry intensity ratio between the nucleus and cytoplasm of ~0.5 (FIG. 11). 740 nm illumination caused an increase of BphP1-mCherry fluorescence in the nucleus (FIG. 4a), resulting in a nucleus/cytoplasm ratio of 1.8. Cells expressing only BphP1-mCherry displayed nucleus/cytoplasm ratios below 0.5, both in darkness and after illumination (FIG. 11). Thus, the light-induced BphP1-PpsR2 interaction caused a ~3.5-fold increase of the BphP1-mCherry signal in nuclei of illuminated cells.

Figure 4C:
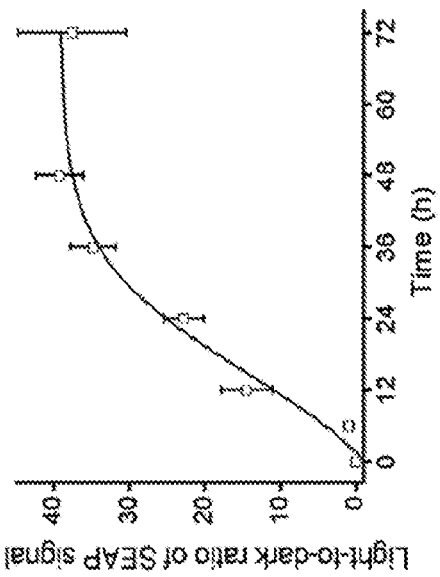
FIG. 4a-4d: Recruitment of BphP1 to the nucleus and light-induced transcription activation. (a) Fluorescence images of HeLa cells co-expressing NLS-PpsR2-mVenus and BphP1-mCherry incubated either in darkness or under irradiation with 740/25 nm pulsed light (30 s On and 180 s Off) of 0.2 mW cm$^{-2}$. Images were acquired at 37° C. using an epifluorescence microscope. Bars, 10 µm. (b) Model of the light-inducible transcription activation system. NIR light converts BphP1 into the Pr state and induces heterodimerization with PpsR2. Nuclear localization signal (NLS) fused with PpsR2 facilitates translocation of the heterodimer to the nucleus where BphP1 fusions interact with tetO DNA repeats via fused TetR. VP16 fused with PpsR2 recruits the transcription initiation complex and triggers transcription of a reporter gene. (c) Kinetics of the light-to-dark ratio of SEAP signal detected in culture media of HeLa cells bearing BphP1-mCherry-TetR co-transfected with NLS-PpsR2-VP16 producing plasmid and pTRE-Tight-SEAP (7×tetO) reporter plasmid after 48 h (n=3; error bars are s.e.m.). (d) Termination of SEAP transcription in HeLa cells with the same constructs as in (c) illuminated with 740/25 nm followed by 60 h of darkness or followed by 12 h of 636/25 nm illumination and then by 48 h of darkness. Data were normalized to SEAP signal of cells irradiated with 740/25 nm for 72 h; the signal from non-irradiated cells was subtracted (n=3; error bars are s.e.m.).
Figure 4D:
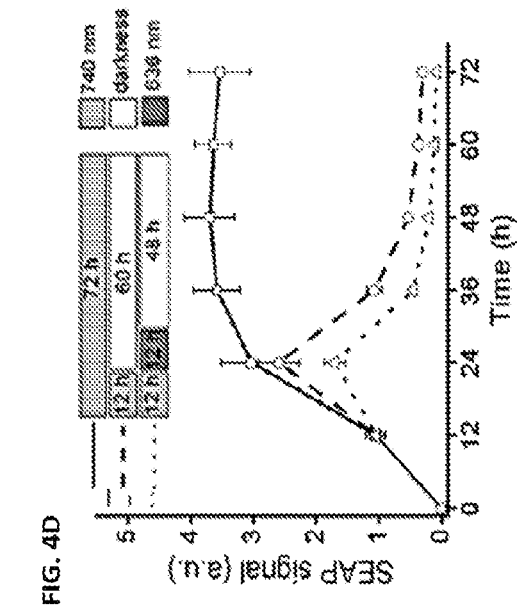
Figure 4A:
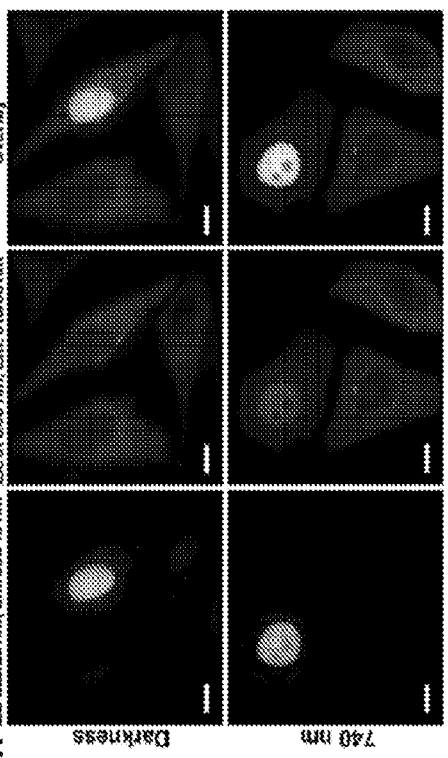
Figure 4B:
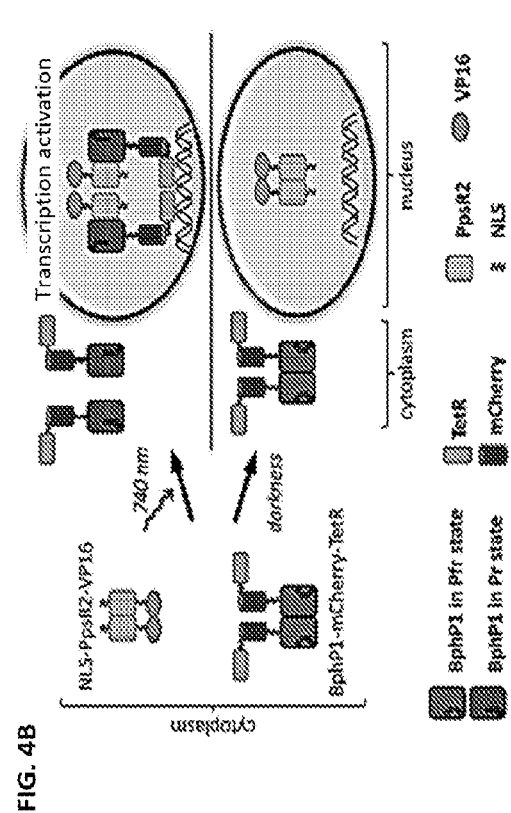
Figure 12A:
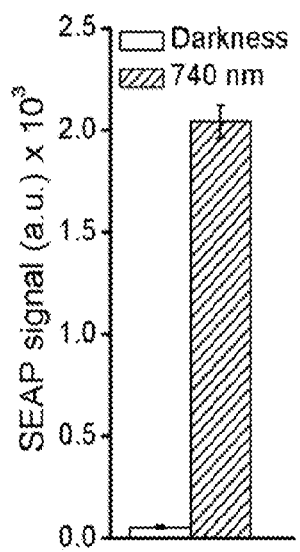
FIG. 12a-12c: Characterization of light-inducible activation of SEAP expression using the TetR-tetO system. (a) SEAP signal detected in culture media of HeLa cells bearing BphP1-mCherry-TetR co-transfected with pCMV-104 and pTRE-Tight-SEAP (7×tetO) reporter plasmid after 48 h in darkness or under 740/25 nm light (n=3; error bars are s.e.m.). (b) Light-to-dark ratio of the SEAP signal shown in (a). (c) The kinetics of SEAP accumulation in culture media of illuminated with 740/25 nm light (dark red) and dark-treated (gray) HeLa cells stably expressing BphP1-mCherry-TetR, transiently co-transfected with pTRE-Tight-SEAP and pCMV-104 plasmids with a plasmids ratio of 1:5 (n=3, error bars are s.e.m.).
Figure 12B:
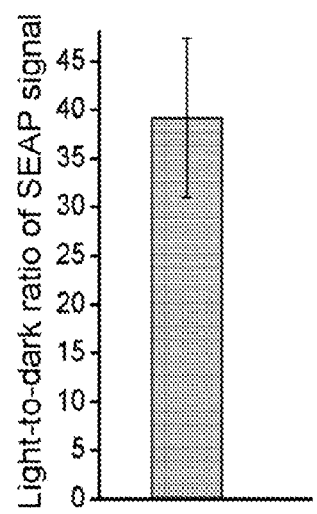
Figure 12C:
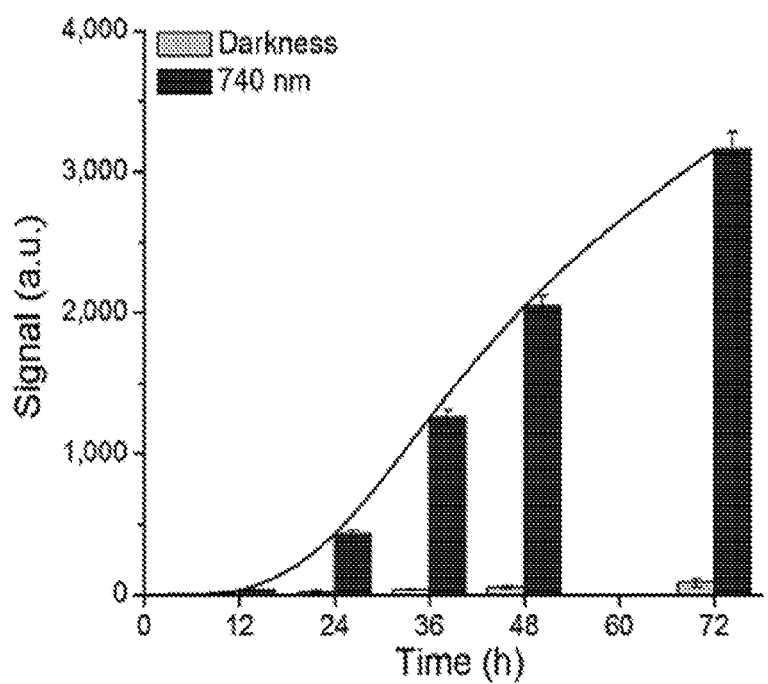
Figure 13:
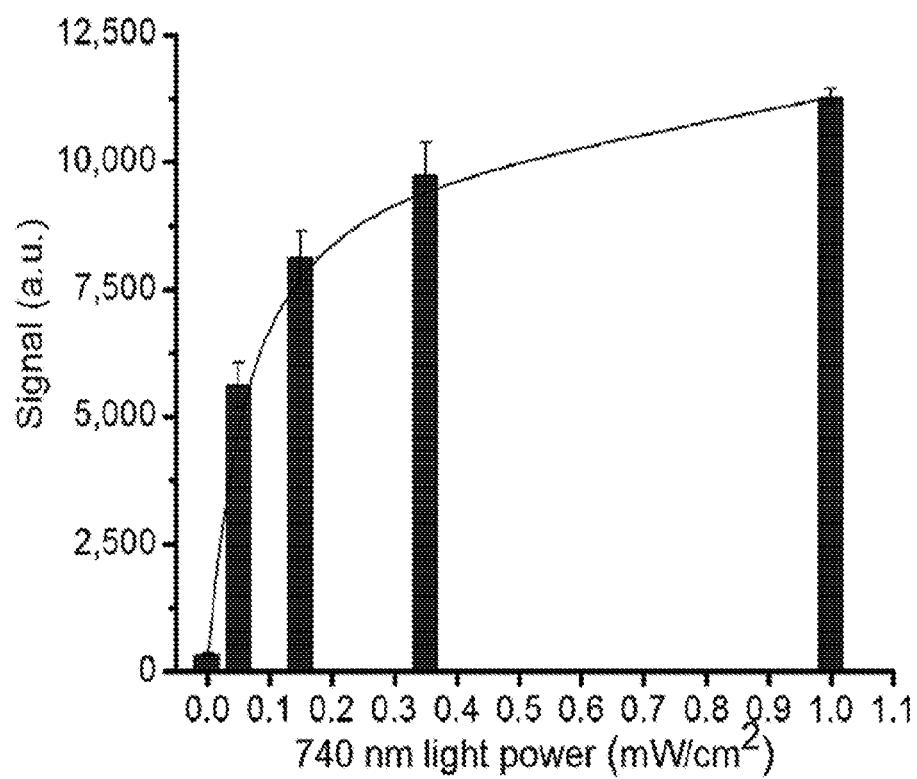
FIG. 13: Dependence of light-induced SEAP expression level on the power of 740 nm light. The light-induced expression of SEAP from the pTRE-Tight-SEAP reporter plasmid. SEAP signal was detected in HeLa cells with BphP1-mCherry-TetR, pTRE-Tight-SEAP and pCMV-104 plasmids. Cells were kept in darkness or under 740/25 nm light at different intensities (n=3, error bars are s.e.m.).

A light-inducible TetR-tetO transcription system. To develop a light-inducible transcription system, the light-induced recruitment of BphP1 to the nucleus was combined with a tetracycline repressor-based system (FIG. 4b). VP16 was fused to the C-terminus of NLS-PpsR2 and the tetracycline repressor (TetR) (ref 46) to BphP1-mCherry. HeLa cells stably expressing BphP1-mCherry-TetR were co-transfected with a plasmid encoding NLS-PpsR2-VP16 and with a pTRE-Tight-SEAP plasmid containing 7×tetO upstream of the SEAP gene. 740 nm illumination increased SEAP levels ~40-fold over the levels in darkness after 48 h (FIG. 12a,b). The time course of SEAP production revealed a ~3-fold SEAP increase after 12 h of 740 nm illumination compared to dark-treated cells (FIG. 12c). SEAP accumulation exhibited a half-time of ~18 h and reached a plateau after 48 h (FIG. 4c, FIG. 12c). SEAP expression level depended on the power of activating light, with SEAP signal observed in cells irradiated with as low as 0.05 mW cm$^{-2}$ (FIG. 13). Similarly, the light-induced BhpP1-PpsP2 interaction caused EGFP expression from a pTRE-Tight-EGFP reporter plasmid resulted in more than 27-fold higher EGFP signal in illuminated over dark-treated cells as detected by flow cytometry (FIG. 14).

Next studied was how fast the light-induced transcriptional activation could be terminated. Cells were illuminated with 740 nm light for 12 h and then kept in darkness. The SEAP reporter production increased ~2.6-fold during the first 12 h in darkness, likely due to pre-accumulation of SEAP mRNA, followed by its subsequent decrease with a half-time of ~8 h (FIG. 4d). It was tested whether 636 nm light would accelerate the termination of transcriptional activation and found that 12 h illumination with 636 nm after the 12 h-illumination period with 740 nm light decreased the SEAP production ~2.3-fold compared to the cells kept in darkness. Moreover, the SEAP decrease in the subsequent darkness after 636 nm illumination also was ~2-fold faster (FIG. 4d). Thus, similar to cell membrane re-localization (FIG. 2), the termination of gene transcription can be accelerated with 636 nm illumination, which causes dissociation of the BphP1-TetR and PpsR2-VP16 complexes in a nucleus.

Next compared were two similar TetR-tetO transcription activation systems, one based on the BphP1-PpsR2 pair and another on a PhyB-PIF6 pair (47), using the same reporter plasmid. The reporter expression was 2-fold higher for the BphP1-PpsR2 than for the PhyB-PIF6 interaction (FIG. 15). Comparison of light propagation for 660 nm and 740 nm wavelengths in various mammalian tissues revealed a substantially more effective penetration of NIR light (FIG. 16), resulting in higher reporter expression at larger tissue depth for the BphP1-PpsR2 system compared to the PhyB-PIF6 system (FIG. 17).

With regard to the results presented in FIG. 16, optical properties of mammalian tissues differ from type to type, and should be regarded as a complex function of different factors. A total absorption of a tissue depends on several parameters, such as an oxygenation degree of hemoglobin, a blood volume, a water content, a fat content, a concentration of endogenous chromophores (bilirubin, melanin, carotene, etc.), a Rayleigh light scattering and a Mie light scattering (48). The tissue optical properties are usually described in terms of three parameters: a scattering coefficient, $\mu_s$, an absorption coefficient, $\mu_a$, and a scattering anisotropy factor, g.

The absorption and scattering coefficients are defined as the probability of absorption or scattering, respectively, per a path-length unit. The third parameter is the scattering distribution in a turbid media, described by the anisotropy factor and obtained by computing the mean cosine of the scattering angle. The value of g, in a scale from −1 to 1, characterizes the direction of the scattering. In most biological tissue, the g value ranges from 0.70 to 0.99, indicating that photons are preferably scattered in the forward direction. Using g factor one can compute a reduced scattering coefficient, which takes into account the anisotropy of scattering in a studied tissue:

$$\mu'_s = (1-g)\mu_s \qquad (1)$$

In a reality, when samples of a bulk tissue are analyzed, the above-mentioned parameters are difficult to evaluate, as these situations are characterized by the occurrence of multiple scattering and absorption events. As the consequence, to characterize optical properties of thick samples another parameter is utilized. An effective attenuation coefficient, $\mu_{\textit{eff}}$, is equal to an inverse of the attenuation length at which the incident spatial irradiance is attenuated by factor of 1/e (~37%). The relation between $\mu_{\textit{eff}}$, $\mu_a$ and $\mu'_s$ is defined as $$\mu_{\textit{eff}} = \sqrt{3\mu_a(\mu_a + \mu'_s)} \qquad (2)$$

The optical properties of different mammalian tissues have been studied by many research groups, and the $\mu_a$ and $\mu'_s$ coefficients were experimentally determined for many tissues (49-54). Thus, it is possible to calculate $\mu_{\textit{eff}}$ using equation (2).

Generally, a relation between absorbed light energy and pathway through which light travels is defined by Beer-Lambert law for thick layers:

$$I(d) = I_0 e^{(-\mu_{\textit{eff}} d)} \qquad (3)$$

where $I_0$ is the initial light intensity, $\mu_{\textit{eff}}$ is the effective attenuation coefficient of tissue at wavelength $\lambda$, and d is the path length of light through the sample.

Using equation (2) and (3) the dependence of relative photon counts for far-red (660 nm) and NIR (740 nm) light on the depth of penetration for 4 mammalian tissues was calculated and plotted, such as brain ($\mu_{\textit{eff}}^{660}=3.2$, $\mu_{\textit{eff}}^{740}=1.76$)[9], breast ($\mu_{\textit{eff}}^{660}=5.5$, $\mu_{\textit{eff}}^{740}=3.13$)[10], muscle ($\mu_{\textit{eff}}^{660}=3$, $\mu_{\textit{eff}}^{740}=1.55$)[5] and bone ($\mu_{\textit{eff}}^{660}=2.24$, $\mu_{\textit{eff}}^{740}=1.77$)[10]. Substantial difference in penetration between 740 nm and 660 nm light at 1 cm depth is observed for the brain and muscle tissues where NIR light penetrates 4-fold more efficiently. The largest difference, ~11-fold, in penetration between 740 nm and 660 nm at 1 cm depth is observed for the breast tissue. This is because of the high level of fat and water content that resulted in the higher $\mu'_s$ for 660 nm light.

Overall, the considerations are consistent with the results published earlier (55). Importantly, in the NIR tissue transparency window the depth of light penetration is highly affected by light-scattering phenomenon: the absorption coefficients for many tissues within 650-900 nm range are ~10-fold lower than the light-scattering coefficients (54).

Light-activation of gene expression in vivo. For activation of gene expression in vivo, stably expressing BphP1-mCherry-TetR HeLa cells were co-transfected with NLS-PpsR2-VP16 and pTRE-Tight-Rluc8 plasmids and subcutaneously injected the cells into the interscapulum area of FVB mice 24 h after co-transfection. Then the animals were either illuminated with 740 nm light or kept in darkness. After 48 h a substantial increase of the Rluc8 signal was detected in the illuminated mice (FIG. 5a) as compared to those kept in darkness. The observed 32-fold activation contrast (FIG. 5b) was similar to that obtained in cell culture experiments (FIG. 12b).

Further compared was the BphP1-PpsR2 system with a blue light-activated LightON system (56). In cultured cells, LightON activation with 470 nm light resulted in 42-fold increase of the Rluc8 signal over the signal in dark treated cells (FIG. 18). However, experiments with subcutaneously injected cells in FVB mice led to only 15-fold Rluc8 activation contrast (FIG. 5c,d). This 2.8-fold drop in Rluc8 production in the LightON system was likely caused by the higher absorbance of 470 nm light than 740 nm light by ~1 mm thick tissue.

To determine whether both the LightOn and our system could potentially be used concurrently, optical crosstalk was tested for in cell culture. Activation of both systems in cultured cells with 470 nm and 740 nm light revealed their low cross-activation. 12-fold higher activation of the LightON system was detected with 470 nm light and 18-fold higher activation of the BphP1-PpsR2 system with 740 nm light (FIG. 19).

For deep tissues studies, the kinetics of light-induced Rluc8 expression in mice was assessed after hydrodynamic transfection (FIG. 5e-h, FIG. 20). After 24 h an increase of Rluc8 signal in livers of 740 nm illuminated mice in comparison with the dark treated animals (FIG. 5f) was detected. After 48 h the Rluc8 signal reached its maximum with a 5.7-fold light-to-dark signal ratio (FIG. 5e,f). Large differences of Rluc8 expression between the illuminated and dark-treated animals were observed up to 72 h after transfection (FIG. 5f). To test the LightON system mice were hydrodynamically transfected with the high amounts of the LightON and reporter plasmids used in the original paper (56) (FIG. 20) or with the amounts similar to those of the BphP1-PpsR2 system (FIG. 5g,h). In the former case, after 470 nm illumination of mice for 24 h, a 1.7-fold increase of the Rluc8 production was observed as compared to the dark treated animals. In the latter case, the signal increase was 2.8-fold (FIG. 5g,h), which was twice lower than that detected for the BphP1-PpsR2 system (FIG. 5e,f). The Rluc8 'bell-shaped' kinetics of the LightON activation in liver observed in both conditions was similar to that reported (58).

Discussion

A novel optogenetic system is disclosed herein based on the light-inducible interaction of bacterial phytochrome BphP1 and its binding partner PpsR2 from R. palustris. This system takes advantage of a high-sensitivity of bacterial phytochromes to NIR light and a unique feature of bacterial phytochromes to incorporate heme-derived BV, which is abundant in mammalian cells and tissues (10), as a chromophore.

The induction of the BphP1-PpsR2 interaction occurs upon photoconversion of BphP1 from a ground Pfr state to the Pr state. Spectroscopic analysis revealed substantial difference in the absorption of Pfr band of BphP1 before and after the Pfr→Pr photoconversion. The photoconversion demonstrates high sensitivity to NIR 740-780 nm light and high rates of the Pfr→Pr transition. Characterization of BphP1-PpsR2 interaction in vitro and in live mammalian cells showed its reversibility in darkness. However, in experiments with light irradiation in Pr absorbing band the BphP1-PpsR2 dissociation was not complete. This might be caused by incomplete Pr→Pfr photoconversion (~80%) of BphP1 with far-red 636 nm light, which is absorbed by both Pr and Pfr states.

It was demonstrated that the BphP1-PpsR2 optogenetic system can be successfully used for activation of several types of cellular processes. First, a light-induced recruitment of one interacting partner to another partner residing in a specific cellular compartment was studied and it was found that using PpsR2-mVenus-CAAX as a partner, 25% of cytoplasmic BphP1 was recruited to plasma membrane.

Excitation light for mVenus and mCherry had negligible overlap with the action spectrum of BphP1, allowing sampling of fluorescence images without altering of the BphP1 state. This approach was also utilized to activate Cdc42 signaling pathway by translocating the DHPH domain of intersectin-1 (24), which normally interacts with Cdc42 at plasma membrane. As a result an increase in cell area caused by lamellipodia formation was observed and changes in cell morphology (FIG. 4) consistent with the Cdc42 activity at lamellipodia (31).

The light-induced targeting approach was extended to the recruitment of BphP1 to a nucleus. To do this, nuclear-localized NLS-PpsR2-mVenus and cytoplasmic BphP1-mCherry constructs were co-expressed. Due to its molecular weight BphP1-mCherry could not undergo passive diffusion through nuclear pores and was localized to the cytoplasm in darkness. NIR light caused formation of complexes between NLS-PpsR2-mVenus and BphP1-mCherry, resulting in substantially higher BphP1 concentration in the nucleus compared to cytoplasm.

The BphP1 nuclear recruitment was also used to activate transcription of several reporter genes downstream of the UAS or tetO binding sites for the light-induced PpsR2-VP16-BphP1-GAL4 and BphP1-tetR-PpsR2-VP16 complexes, respectively. This resulted in up to 40-fold increase in the reporter expression. The light-induced transcription was reversible in darkness. Furthermore, an irradiation with far-red light accelerated the termination of transcription by 2-fold, allowing its more precise control. Moreover, Cre recombinase expressed using this technique enabled substantial DNA recombination. In future studies, a combination of the Cre-mediated DNA recombination with the NIR light-control of Cre expression should provide a powerful non-invasive approach for genome editing in live animals (32).

These NIR light-inducible transcription approaches are easily transferable to model organisms genetically constructed to utilize the GAL4-UAS (28) and tetR-tetO (29) systems to enable protein expression in cells and tissues in spatiotemporal manner. Moreover, the light inducible tetR-based system will allow to avoid such drawbacks of consumption of tetracycline and its derivatives by experimental animals, as inhibition of proliferation, angiogenesis and cell migration, and induction of apoptosis in cancer models (33).

For in vivo applications, optogenetic systems sensing NIR light are required due to its deep tissue penetration and reduced phototoxicity compared to blue light utilizing LOV and cryptochrome systems. Majority of currently available far-red optogenetic systems are based on a PPI between plant phytochrome PhyB and its interacting partner PIF6 (3, 9, 34). These systems become active in response to far-red light peaked at 660 nm, whereas BphP1-PpsR2 interaction can be set off by NIR light with wavelengths of 740-780 nm. Moreover, a use of the PhyB-PIF6 systems is limited by the requirement to either supply exogenous phycocyanobilin chromophore (5, 6) or to produce it in cells by co-expressing several enzymes of bacterial origin (35), thus, affecting cellular metabolism.

Two similar TetR-tetO systems were compared, one based on the BphP1-PpsR2 described above and another system (9) based on the PhyB-PIF6 pair using the same pTRE-Tight-SEAP reporter plasmid. The BphP1-PpsR2 expressing cells were illuminated with 740 nm while the cells with the PhyB(1-650)-VP16-NLS and tetR-PIF6 constructs were illuminated with 660 nm and also supplemented with 15 µM of phycocyanobilin. Dependence of the efficiency of reporter activation on the light intensity was rather similar for the BphP1-PpsR2 and the PhyB-PIF6 systems and decreased with the attenuation of the light power. However, comparison of light propagation for 740 nm and 660 nm wavelengths in various mammalian tissues reveals substantially more effective penetration of NIR light. This results in much slower decrease of the level of reporter production with the tissue depth for the BphP1-PpsR2 system as compared to the PhyB-PIF6 system.

The in vivo comparison of transcription activation by the blue-light driven LightON system and NIR-light activated BphP1-PpsR2 system revealed a higher efficiency of the latter one at light intensities of ≤5 mW cm$^{-2}$, which are compliant with safety regulations. These light intensities caused a smaller increase of the Rluc8 signal in a deep-seated liver in the 470 nm illuminated animals as compared to the Rluc8 signal obtained with 90 mW cm$^{-2}$ illumination used in the original LightON paper (56).

In summary, the BphP1-PpsR2 light-controllable PPI was characterized both in vitro and in live mammalian cells and demonstration shown of the use of this light-sensitive pair as a novel optogenetic system for subcellular protein targeting, induction of intracellular enzymatic activity, activation of gene expression and control of DNA recombination. The BphP1-PpsR2 system is orthogonal to mammalian cells and minimally interferes with cellular metabolism.

Materials and Methods

Construction of bacterial and mammalian plasmids: A gene encoding RpBphP1 from *R. palustris* was kindly provided by E. Giraud. A gene encoding RpPpsR2 from *R. palustris* was kindly provided by M. Papiz. A DHPH domain of human intersectin-1 was PCR amplified from a pAL189 plasmid (Addgene #22278)(3). An mRuby2 gene was PCR amplified from a pcDNA3-mRuby2 plasmid (Addgene #40260)(36) A DNA binding domain of the transcription factor GAL4 from *S. cerevisiae* and a transactivation domain of transactivating tegument protein VP16 from *H. simplex* were PCR amplified from a pGV-2ER plasmid (Systasy). A reporter plasmid pG5-EGFP was purchased from Systasy. A SEAP gene was PCR amplified from a pKM611 plasmid kindly provided by W. Weber. A plasmid pKM022 encoding PhyB(1-650) was obtained by mutagenesis, using the pKM020 plasmid as a template (9). A Cre recombinase gene was PCR amplified from a pBS185-CMV-Cre (Addgene #11916) (37). A tetR gene (residues 1-207) that binds DNA in the absence of tetracycline/doxycycline was PCR amplified from a pTet-Off vector (Clontech). The reporter plasmids pTRE-Tight-EGFP, pTRE-Tight-SEAP and pTRE-Tight-Cre were obtained by cloning of the EGFP, SEAP and Cre genes, respectively, into a pTRE-Tight2 vector (Addgene #19407). To develop stable preclonal cell mixtures of HeLa cells, plasmids encoding a transposase SB100X, pCMV(CAT)T7-SB100 (Addgene #34879)(38) and transposon bearing plasmids pT2/SVNeo and pT2/BH (Addgene #26553 and #26556)(39) were utilized. A reporter plasmid pCALNL-GFP was obtained from Addgene (#13770)(40).

For bacterial expression of the BphP1, BphP1-mRuby2 and PpsR2-mRuby2 proteins, a pBAD/His-D, a pBAD/His-B (Life Technologies-Invitrogen) and a pET22b (Novagen) vectors were used, respectively. In the pET22b vector an N-terminal pelB signal was replaced with a Strep-tag-II.

Mammalian expression plasmids were based either on a pEGFP-N1 vector (Clontech), having either a standard CMV promoter or a truncated to CMVd1 promoter, or on a pFC15K vector (Promega) with the truncated CMVd1 promoter. The flexible linkers of 10 (-DSAGSAGSAG-) (SEQ ID NO:1), 16 (-SAGGSAGGSAGGSAGG-) (SEQ ID NO:2), 20 (-SAGGSAGGSAGGSAGGSAGG-) (SEQ ID NO:3) or 24 (-SGGGSGGGSGGGSGGGSGGGSGGG-) (SEQ ID NO:4) amino acids, a C-terminal membrane-localization -CAAX signal from Kras4B (-KKKKKK-SKTKCVIM) (SEQ ID NO:5), a nuclear localization signal of nuclear cap-binding protein subunit 1 (MSRRRHSY-ENDGGQPHKRRK-) (SEQ ID NO:6), a T2A peptide (-EGRGSLLTCGDVEENPGP-) (SEQ ID NO:7), and a Strep-tag-II (-WSHPQFEK-) (SEQ ID NO:8) were added by oligonucleotide annealing. The designed plasmids are summarized in Table 2.

Yvon) equipped with a 600 nm shortpass filter before detector was used. A photoconversion of BphP1 containing proteins was performed with 740/25 nm and 636/20 nm custom assemble LED sources in quartz microcuvettes (Starna Cells). A determination of action spectrum was performed by measurement of changing in absorbance of Pfr state BphP1 at 780 nm upon illumination with photoconversion light. As a source of light the FluoroMax-3 spectrofluorometer was used. The illumination time was normalized to total amount of irradiated light energy, measured

TABLE 2

A list of the plasmids constructed in this study.

| Plasmid | FIG. | Vector backbone | Promoter | Insert |
|---|---|---|---|---|
| pKA-100 | 1, 6-8 | pBAD/His-D | PBAD | BglII-BphP1-EcoRI |
| pKA-101 | 7 | pBAD/His-B | PBAD | BglII-BphP1-EcoRI-10aaLinker-SpeI-mRuby2-HindIII |
| pKA-138.2 | 1, 7 | pET-22b | T7 | NdeI-Strep-tag II-NcoI-PpsR2-HindIII-20aaLinker-AgeI-mRuby2-XhoI-His-tag |
| pKA-140 | 2 | pEGFP-N1 | CMV | KpnI-PpsR2(C439S)-HindIII-20aaLinker-AgeI-mVenus-NheI-Kras4BCT-NotI |
| pKA-141 | 2, 9 | pFC15K | CMVd1 | NheI-BphP1-EcoRI-10aaLinksr-SpeI-mCherry-XbaI |
| pKA-142 | 2, 3, 9, 10 | pFC15K | CMVd1 | AsiSI-PpsR2(C439S)-HindIII-20aaLinker-AgeI-mVenus-NheI-Kras4BCT-NotI |
| pKA-144 | 3, 10 | pFC15K | CMVd1 | NheI-BphP1-EcoRI-10aaLinker-SpeI-mCherry-BsrGI-20aaLinker-XbaI-IntersectinDHPH-NotI |
| pKA-147 | 3 | pFC15K | CMVd1 | AsiSI-mVenus-NheI-Kras4BCT-NotI |
| pCMV-160 | 4, 11 | pEGFP-N1 | CMV | AsiSI-NLS-AgeI-PpsR2(C439S)-HindIII-20aaLinker-AgeI-mVenus-XbaI |
| pT2/SVNeo-103 | 4, 5, 11-15, 18 | pT2/SVNeo | CMVd1 | IRDR-CMVd1-NheI-BphP1-EcoRI-10aaLinker-SpeI-mCherry-BsrGI-24aaLinker-XbaI-TetR-NotI-NeoR-IRDR |
| pKA-207I10 | 5 | pIRES-EGFP | CMV | NheI-NLS-AgeI-PpsR2-HindIII-20aaLinker-NcoI-VP16-BglII-IRESv10-NcoI-BphP1-EcoRI-10aaLinker-mCherry-TetR-NotI |
| pCMV-104 | 4, 5, 12-15, 18 | pEGFP-N1 | CMV | AsiSI-NLS-AgeI-PpsR2(C439S)-HindIII-20aaLinker-AgeI-VP16-XbaI |
| pTRE-Tight-SEAP | 4, 12, 13 15 | pTRE-Tight2 | $CMV_{min}$ | XhoI-7xtet-responsive element-$P_{minCMV}$-BamHI-SEAP-NotI |
| pTRE-Tight-EGFP | 14 | pTRE-Tight2 | $CMV_{min}$ | XhoI-7xtet-responsive element-$P_{minCMV}$-BamHI-EGFP-NotI |
| pTRE-Tight-Rluc8 | 5, 19 | pTRE-Tight2 | $CMV_{min}$ | XhoI-7xtet-responsive element-$P_{minCMV}$-BamHI-Rluc8-NotI |
| pU5-Rluc8 | 5, 18-20 | pU5-mCherry | min TATA-box promoter | 5xGAL4-binding UAS-minimal promoter-HindIII-Rluc8-BamHI |

Protein expression and purification: BphP1 and BphP1-mRuby2 proteins with polyhistidine tags on the N-terminus were expressed in LMG194 bacterial cells (Life Technologies-Invitrogen) containing a pWA23h plasmid encoding heme oxygenase for biliverdin synthesis in *E. coli* (12). The bacterial cells were grown in RM medium supplemented with ampicillin, kanamycin and 0.02% rhamnose for 6-8 h followed by an induction of the protein expression by adding of 0.002% arabinose. The proteins were purified using a Ni-NTA agarose (Qiagen). The PpsR2 and PpsR2-mVenus proteins with a Strep-tag-II at the N-terminus and a polyhistidine tag at the C-terminus was expressed in BL21(DE3) bacterial cells grown in LB medium supplemented with ampicillin for 6 h, followed by an induction of a protein expression with 250 µM IPTG. The proteins were first purified with a Ni-NTA agarose (Qiagen) followed by purification with a Strep-Tactin sepharose (IBA Lifesciences).

In vitro characterizations of BphP1 properties: For absorbance measurements, a Hitachi U-2000 spectrophotometer was used. For fluorescence measurements of mRuby2 fusions, a FluoroMax-3 spectrofluorometer (Horiba-Jobin with a PM100 optical powermeter equipped with a S130A sensor (ThorLabs) at the respective wavelength. A half-time of Pr→Pfr transition (or dark relaxation) was measured by registering of absorbance at 780 nm after 5 min illumination of samples with 740/25 nm. Samples containing fixed quantity of BphP1 (5 µM) and various quantities of PpsR2 (0-5 µM) were pre-incubated in darkness for 30 min. Reversible dark relaxation cycles were obtained by registration 780 nm absorbance of protein mixture at BphP1:PpsR2 molar ratio of 8:1. To study changes in mRuby2 fluorescence due to FRET between the PpsR2-mRuby2 fusion and the Pr state of BphP1, the proteins (2.5 µM each) were pre-incubated in darkness for 30 min and then transferred to a microcuvette. An mRuby2 fluorescence intensity was registered each 30 s with excitation 545/2 nm and emission 585/10 nm. All spectroscopic measurements were performed at a room temperature in PBS.

Mammalian cell culture: HeLa cells were grown in DMEM medium supplemented with 10% FBS, penicillin-streptomycin mixture and 2 mM glutamine (all from Life Technologies-Invitrogen) at 37° C. For experiments $10^5$ cells were plated on a pre-coated with ECL mixture (EMD-Millipore) 35 mm glass-bottom culture dishes (MatTek). Transient cell transfections were performed using an Effectene reagent (Qiagen).

Preclonal mixtures of HeLa cells were obtained using the plasmid-based Sleeping Beauty transposon system. For this, the desired for integration into genome sequences were cloned into the transposon bearing plasmids pT2/BH or pT2/SVNeo and co-transfected with a plasmid encoding a hyperactive transposase SB100X. Cells were further selected with 700 µg/ml of G418 antibiotic for two weeks and enriched using a FACSAria sorter (BD Biosciences), resulting in the preclonal HeLa cell mixtures stably expressing NLS-VP16-PpsR2-T2A-BphP1-mCherry-GAL4 or BphP1-mCherry-tetR.

For light-induced re-localization to plasma membrane, HeLa cells were transiently co-transfected with pKA-140 or pKA-142 and pKA-141 plasmids in 1:1 ratio. For light-induced cytoskeletal rearrangement, cells were co-transfected with pKA-142 (or pKA-147) and pKA-144 plasmids in 1:2 ratio. The cell light-activation and imaging were typically performed 48 h after the transfection. For light-induced nuclear re-localization, HeLa cells stably expressing BphP1-mCherry-tetR were transiently transfected with pCMV-160. To study transcription activation, HeLa cells stably expressing NLS-VP16-PpsR2-T2ABphP1-mCherry-GAL4 were transfected with a pG5-EGFP for light-induced EGFP expression or with a pG5-SEAP for kinetic studies. To study light-induced transcription activation in tetR-based system HeLa cells stably expressing BphP1-mCherry-tetR were co-transfected with pCMV-104 and either pTRE-Tight-EGFP or pTRE-Tight-SEAP plasmids in 5:1 ratio. To study Cre-driven expression of EGFP HeLa cells stably expressing BphP-mCherry-tetR were co-transfected with pTRE-Tight-Cre, pCALNL-GFP and pAS-104 plasmids in 0.6:1:2 ratio. To compare the PhyB-PIF6 system with the BphP1-PpsR2 system, HeLa cells were transfected with pKM022 and pTRE-Tight-SEAP plasmids in 2:1 ratio. All procedures after the transfection were performed as described in the respective PhyB-PIF6 paper (9).

Cell light-activation and imaging: Imaging was performed using an Olympus IX81 inverted epifluorescence microscope equipped with a 200 W metal halide arc lamp (Lumen 220PRO, Prior) and a 60×1.35 NA oil immersion objective lens (UPlanSApo, Olympus). During imaging HeLa cells were incubated in a cell imaging medium (Life Technologies-Invitrogen) and kept at 37° C. Yellow (523/20 nm exciter and 565/40 nm emitter) and red (570/30 nm exciter and 615/30 nm emitter) channel filter sets (Chroma) were used for detection of mVenus and mCherry fluorescence, respectively. The Pfr→Pr photoconversion of BphP1 was done by illuminating with 740/40 nm filter (Chroma).

For Pfr→Pr re-localization assay, HeLa cells were exposed to 740/40 nm for 3 min while imaged every 15 s. An intensity of activation light was 0.9 mW/cm$^2$. To quantify mCherry fluorescence in cell cytoplasm during BphP1 dark relaxation, HeLa cells were imaged every 3 min during 24 min, starting immediately after the Pfr→Pr photoconversion. Intensity profile of mCherry fluorescence through cell was determined using an ImageJ v.1.46f software. Intensity of mCherry fluorescence in cytoplasm and nucleus was measured using a SlideBook v.4.2.09.

To study light-induced cytoskeletal rearrangements, the Pfr→Pr photoconversion was done by illuminating cells using 740/40 nm filter for 3 min and imaged every 15 s, followed by further maintaining of BphP1 in the Pr state by illuminating with 740/40 nm for 15 s every minute and imaged every 60 s. An intensity of activation light was 0.2 mW/cm$^2$. The total time of cells imaging was 30 min. The light power densities were measured at a back focal plane of a 60×1.35 NA objective lens. Membrane-localized mVenus was used for determination of cell area. The data were analyzed using an ImageJ v.1.46f software.

Unless otherwise indicated, a light-induced transcription activation HeLa cells was performed with 740/25 nm LED source at 1.0 mW cm$^{-2}$ using the 30 s On and 180 s Off cycle in $CO_2$ incubator at 37° C. Time of illumination varied in different experiments. For nuclear localization and EGFP or SEAP transcription activation experiments, cells were illuminated for 24 and 48 h, respectively. For kinetic studies of SEAP accumulation in culture media, 3 different illumination regimes were used: 72 h of 740/25 nm; 12 h of 740/25 nm followed by 60 h of darkness; and 12 h of 740/25 nm followed by 12 h of 636/20 nm followed by 38 h of darkness. To measure light sensitivity of activation of SEAP expression, HeLa cells were irradiated with either 740/25 (with BphP1-PpsR2) or 660/20 nm (with PhyB-PIF6) light of various power densities (5-1000 µW cm$^{-2}$). Light power densities and durations of illumination were converted to photons counts.

Light-induced LightON transcription activation of Rluc8 in HeLa cells was performed as described in the original paper (56). In brief, HeLa cells were transfected with pGAVPO and pU5-Rluc8 plasmids in 1:1 ratio. Then cells were kept in darkness for 10 h. After change of culture medium, the cells were continuously illuminated with a 470/15 nm LED array (LuxeonStar) of 1 mW cm$^{-2}$ or remained in a darkness for 48 h before analysis. For an analysis, the cells were resuspended in PBS and disrupted by freezing-thawing. An Rluc8 bioluminescence signal was measured in supernatants after adding of 5 µM h-coelenterazine (NanoLight Technology). A signal was detected using an IVIS Spectrum instrument (PerkinElmer/Caliper Life Sciences) and analyzed using Living Image 3.0 software (PerkinElmer/Caliper Life Sciences).

Flow cytometry analysis: Flow cytometry analysis of a light-induced EGFP expression and a Cre mediated EGFP expression was performed 48 h after the HeLa cell transfection using a LSRII flow cytometer (BD Biosciences) equipped with a 488 nm laser and a 530/40 nm emission filter and with a 561 nm laser and 610/20 nm emission filter. To calculate an efficiency of the light-induced EGFP expression, a mean fluorescent intensity of EGFP positive cells was multiplied by a number of the positive cells, resulting in the total amount of synthesized proteins. In contrast, for a Cre mediated EGFP expression, the EGFP positive cells were counted only. Gates for counting of EGFP positive cells were set using non-transfected cells as a negative control. Typically, the cell samples were triplicated. Minimally, $5 \times 10^4$ cells were analyzed per a sample. The data were analyzed using a FACSDiva v. 6.1.3 and a FlowJo v. 7.6.2 software.

Secreted alkaline phosphatase assay: For SEAP detection in culture media, a Great EscApe fluorescent SEAP Assay kit (Clontech) was used. 25 µl aliquots of cell culture media from wells of a 6-well plate or a 12-well plate were collected at each time point and stored at −20° C. For kinetics studies, a culture medium was changed with a fresh medium at each time point. A fluorescence intensity of the SEAP reaction product was measured using the SpectraMax-M2 plate reader.

Light-activation and imaging in mice. The FVB 2-3 month old female mice (National Cancer Institute, NIH) of 20-25 g body weight were used for in vivo comparison of the LightON and BphP1-PpsR2 systems. To compare an efficiency of the light-induced transcription activation, HeLa cells bearing either the LightON system or the BphP1-PpsR2 system were injected subcutaneously in the interscapular area of FVB mice. For better illumination the fur on the back was removed using a depilatory cream. For the LightON system, HeLa cells were co-transfected with the pGAVPO and pU5-Rluc8 plasmids in a 1:1 ratio, and for the BphP1-PpsR2 system, HeLa cells stably expressing BphP1-mCherry-TetR were co-transfected with the plasmid encoding NLS-PpsR2-VP16 and the pTRE-Tight-Rluc8 reporter plasmid in a 5:1 ratio. For both systems, the $3\times10^6$ HeLa cells in 100 µl of RPMI-1640 media supplemented with 2 mM L-glutamine were injected subcutaneously 24 h after the transfection. All manipulations with cells before and during the injection were performed under a 640 nm safelight for the LightON system and under a 530 nm safelight for the BphP1-PpsR2 system. After cells injection, mice were placed in transparent cages with the top illumination of either the 470/15 nm LED array or the 740/25 nm LED array, respectively. Intensities of 470/15 nm light and 740/25 nm light were the same and equal to 1 mW cm$^{-2}$. Control mice after injection of the cells were kept in darkness in conventional cages. Animals were continuously illuminated or kept in darkness for 48 h, and every 12 h were released and fed for 30 min. Each experimental group contained 3 mice.

For hydrodynamic transfection into liver (57), the Swiss Webster 2-3 month old female mice (National Cancer Institute, NIH) with body weight of 22-25 g were used. For the BphP1-PpsR2 system, 50 µg of the pKA-207I10 plasmid and 5 µg of the pTRE-Tight-Rluc8 reporter plasmid in 2.5 ml of PBS were intravenously injected through a tail vein. For hydrodynamic transfection by the LightON system, the plasmid amounts either indicated in the original paper (56) were used (10 µg of the pGAVPO plasmid and 300 µg of the pU5-Rluc8 plasmid) or similar to those used for the BphP1-PpsR2 system (50 µg of the pGAVPO plasmid and 5 µg of the pU5-Rluc8 plasmid). The mice were placed in transparent cages and illuminated from the bottom with the 470/15 nm LED array and the 740/25 nm LED array, respectively. Intensity of the both activation light was the same and equal to 5 mW cm$^{-2}$. For better illumination and imaging the belly fur was removed using a depilatory cream. Control animals were kept in conventional cages in complete darkness. Animals were continuously illuminated or kept in darkness for 72 h, and every 12 h were released and fed for 30 min. Each experimental group contained 3 mice.

For bioluminescence detection, 48 h after the HeLa cells injection or every 24 h after the hydrodynamic transfection of livers the animals were imaged using an IVIS Spectrum instrument (Perkin Elmer/Caliper Life Sciences) in luminescence mode with an open emission filter. Throughout the imaging, animals were maintained under anesthesia with 1.5% vaporized isoflurane. Prior to imaging, 80 µg of Inject-A-Lume CTZ native (NanoLight Technology) were intravenously injected through a retro-orbital vein. Data were analyzed using Living Image 3.0 software (Perkin Elmer/Caliper Life Sciences).

REFERENCES

1. Stierl, M. et al. Light modulation of cellular cAMP by a small bacterial photoactivated adenylyl cyclase, bPAC, of the soil bacterium Beggiatoa. *J Biol Chem* 286, 1181-1188 (2011).
2. Ni, M., Tepperman, J. M. & Quail, P. H. Binding of phytochrome B to its nuclear signalling partner PIF3 is reversibly induced by light. *Nature* 400, 781-784 (1999).
3. Levskaya, A., Weiner, O. D., Lim, W. A. & Voigt, C. A. Spatiotemporal control of cell signalling using a light-switchable protein interaction. *Nature* 461, 997-1001 (2009).
4. Weissleder, R. & Ntziachristos, V. Shedding light onto live molecular targets. *Nat Med* 9, 123-128 (2003).
5. Ulijasz, A. T. & Vierstra, R. D. Phytochrome structure and photochemistry: recent advances toward a complete molecular picture. *Curr Opin Plant Biol* 14, 498-506 (2011).
6. Piatkevich, K. D., Subach, F. V. & Verkhusha, V. V. Engineering of bacterial phytochromes for near-infrared imaging, sensing, and light-control in mammals. *Chem Soc Rev* 42, 3441-3452 (2013).
7. Wagner, J. R. et al. Mutational analysis of Deinococcus radiodurans bacteriophytochrome reveals key amino acids necessary for the photochromicity and proton exchange cycle of phytochromes. *J Biol Chem* 283, 12212-12226 (2008).
8. Essen, L. O., Mailliet, J. & Hughes, J. The structure of a complete phytochrome sensory module in the Pr ground state. *Proc Natl Acad Sci USA* 105, 14709-14714 (2008).
9. Muller, K. et al. A red/far-red light-responsive bi-stable toggle switch to control gene expression in mammalian cells. *Nucleic Acids Res* 41, e77 (2013).
10. Tran, M. T. et al. In vivo image analysis using iRFP transgenic mice. *Experimental animals/Japanese Association for Laboratory Animal Science* 63, 311-319 (2014).
11. Shcherbakova, D. M. & Verkhusha, V. V. Near-infrared fluorescent proteins for multicolor in vivo imaging. *Nat Methods* 10, 751-754 (2013).
12. Piatkevich, K. D., Subach, F. V. & Verkhusha, V. V. Far-red light photoactivatable near-infrared fluorescent proteins engineered from a bacterial phytochrome. *Nat Commun* 4, 2153 (2013).
13. Filonov, G. S. & Verkhusha, V. V. A near-infrared BiFC reporter for in vivo imaging of protein-protein interactions. *Chem Biol* 20, 1078-1086 (2013).
14. Auldridge, M. E. & Forest, K. T. Bacterial phytochromes: more than meets the light. *Crit Rev Biochem Mol Biol* 46, 67-88 (2011).
15. Wagner, J. R., Zhang, J., Brunzelle, J. S., Vierstra, R. D. & Forest, K. T. High resolution structure of Deinococcus bacteriophytochrome yields new insights into phytochrome architecture and evolution. *J Biol Chem* 282, 12298-12309 (2007).
16. Rockwell, N. C. & Lagarias, J. C. A brief history of phytochromes. *Chemphyschem* 11, 1172-1180 (2010).
17. Burgie, E. S. & Vierstra, R. D. Phytochromes: An Atomic Perspective on Photoactivation and Signaling. *Plant Cell* 26, 4568-4583 (2014).
18. Ryu, M. H. & Gomelsky, M. Near-infrared Light Responsive Synthetic c-di-GMP Module for Optogenetic Applications. *ACS Synth Biol* (2014).
19. Gasser, C. et al. Engineering of a red-light-activated human cAMP/cGMP-specific phosphodiesterase. *Proc Natl Acad Sci USA* 111, 8803-8808 (2014).
20. Ryu, M. H. et al. Engineering adenylate cyclases regulated by near-infrared window light. *Proc Natl Acad Sci USA* 111, 10167-10172 (2014).

21. Rottwinkel, G., Oberpichler, I. & Lamparter, T. Bathy phytochromes in rhizobial soil bacteria. *J Bacteriol* 192, 5124-5133 (2010).
22. Kojadinovic, M. et al. Dual role for a bacteriophytochrome in the bioenergetic control of *Rhodopseudomonas palustris*: enhancement of photosystem synthesis and limitation of respiration. *Biochim Biophys Acta* 1777, 163-172 (2008).
23. Bellini, D. & Papiz, M. Z. Structure of a bacteriophytochrome and light-stimulated protomer swapping with a gene repressor. *Structure* 20, 1436-1446 (2012).
24. Hussain, N. K. et al. Endocytic protein intersectin-1 regulates actin assembly via Cdc42 and N-WASP. *Nat Cell Biol* 3, 927-932 (2001).
25. Hall, A. Rho GTPases and the actin cytoskeleton. *Science* 279, 509-514 (1998).
26. Nobes, C. D. & Hall, A. Rho, rac, and cdc42 GTPases regulate the assembly of multimolecular focal complexes associated with actin stress fibers, lamellipodia, and filopodia. *Cell* 81, 53-62 (1995).
27. Sadowski, I., Ma, J., Triezenberg, S. & Ptashne, M. GAL4-VP16 is an unusually potent transcriptional activator. *Nature* 335, 563-564 (1988).
28. Mallo, M. Controlled gene activation and inactivation in the mouse. *Front Biosci* 11, 313-327 (2006).
29. Schönig, K., Bujard, H. & Gossen, M. The power of reversibility regulating gene activities via tetracycline-controlled transcription. *Methods Enzymol* 477, 429-453 (2010).
30. Nagy, A. Cre recombinase: the universal reagent for genome tailoring. *Genesis* 26, 99-109 (2000).
31. Guntas, G. et al. Engineering an improved light-induced dimer (iLID) for controlling the localization and activity of signaling proteins. *Proc Natl Acad Sci USA* 112, 112-117 (2015).
32. Deng, C. X. Conditional knockout mouse models of cancer. *Cold Spring Harb Protoc* 2014, 1217-1233 (2014).
33. Albanese, C., Hulit, J., Sakamaki, T. & Pestell, R. G. Recent advances in inducible expression in transgenic mice. *Semin Cell Dev Biol* 13, 129-141 (2002).
34. Toettcher, J. E., Weiner, O. D. & Lim, W. A. Using optogenetics to interrogate the dynamic control of signal transmission by the Ras/Erk module. *Cell* 155, 1422-1434 (2013).
35. Müller, K. et al. Synthesis of phycocyanobilin in mammalian cells. *Chem Commun (Camb)* 49, 8970-8972 (2013).
36. Lam, A. J. et al. Improving FRET dynamic range with bright green and red fluorescent proteins. Nat Methods 9, 1005-1012 (2012).
37. Sauer, B. & Henderson, N. Targeted insertion of exogenous DNA into the eukaryotic genome by the Cre recombinase. New Biol 2, 441-449 (1990).
38. Mátés, L. et al. Molecular evolution of a novel hyperactive Sleeping Beauty transposase enables robust stable gene transfer in vertebrates. Nat Genet 41, 753-761 (2009).
39. Cui, Z., Geurts, A. M., Liu, G., Kaufman, C. D. & Hackett, P. B. Structure-function analysis of the inverted terminal repeats of the sleeping beauty transposon. J Mol Biol 318, 1221-1235 (2002).
40. Matsuda, T. & Cepko, C. L. Controlled expression of transgenes introduced by in vivo electroporation. Proc Natl Acad Sci USA 104, 1027-1032 (2007).
41. Motta-Mena, L. B. et al. An optogenetic gene expression system with rapid activation and deactivation kinetics. *Nat Chem Biol* 10, 196-202 (2014).
42. Kawano, F., Suzuki, H., Furuya, A. & Sato, M. Engineered pairs of distinct photoswitches for optogenetic control of cellular proteins. *Nat Commun* 6, 6256 (2015).
43. Hussain, N. K. et al. Endocytic protein intersectin-1 regulates actin assembly via Cdc42 and N-WASP. *Nat Cell Biol* 3, 927-932 (2001).
44. Hall, A. Rho GTPases and the actin cytoskeleton. *Science* 279, 509-514 (1998).
45. Nobes, C. D. & Hall, A. Rho, rac, and cdc42 GTPases regulate the assembly of multimolecular focal complexes associated with actin stress fibers, lamellipodia, and filopodia. *Cell* 81, 53-62 (1995).
46. Orth, P., Schnappinger, D., Hillen, W., Saenger, W. & Hinrichs, W. Structural basis of gene regulation by the tetracycline inducible Tet repressor-operator system. *Nat Struct Biol* 7, 215-219 (2000).
47. Muller, K. et al. A red/far-red light-responsive bi-stable toggle switch to control gene expression in mammalian cells. *Nucleic Acids Res* 41, e77 (2013).
48. Stierl, M. et al. Light modulation of cellular cAMP by a small bacterial photoactivated adenylyl cyclase, bPAC, of the soil bacterium Beggiatoa. *J Biol Chem* 286, 1181-1188 (2011).
49. Taslimi, A. et al. An optimized optogenetic clustering tool for probing protein interaction and function. *Nat Commun* 5, 4925 (2014).
50. Lee, S. et al. Reversible protein inactivation by optogenetic trapping in cells. *Nat Methods* 11, 633-636 (2014).
51. Ni, M., Tepperman, J. M. & Quail, P. H. Binding of phytochrome B to its nuclear signalling partner PIF3 is reversibly induced by light. *Nature* 400, 781-784 (1999).
52. Levskaya, A., Weiner, O. D., Lim, W. A. & Voigt, C. A. Spatiotemporal control of cell signalling using a light-switchable protein interaction. *Nature* 461, 997-1001 (2009).
53. Gomez, E. J., Gerhardt, K., Judd, J., Tabor, J. J. & Suh, J. Light-activated nuclear translocation of adeno-associated virus nanoparticles using phytochrome B for enhanced, tunable, and spatially programmable gene delivery. *ACS Nano* 10, 225-237 (2016).
54. Weissleder, R. & Ntziachristos, V. Shedding light onto live molecular targets. *Nat Medicine* 9, 123-128 (2003).
55. Ulijasz, A. T. & Vierstra, R. D. Phytochrome structure and photochemistry: recent advances toward a complete molecular picture. *Curr Opin Plant Biol* 14, 498-506 (2011).
56. Wang, X., Chen, X. & Yang, Y. Spatiotemporal control of gene expression by a light-switchable transgene system. *Nat Methods* 9, 266-269 (2012).
57. Liu, F., Song, Y. & Liu, D. Hydrodynamics-based transfection in animals by systemic administration of plasmid DNA. *Gene Ther* 6, 1258-1266 (1999).
58. Chen, X., Li, T., Wang, X. & Yang, Y. A light-switchable bidirectional expression module allowing simultaneous regulation of multiple genes. *Biochem Biophys Res Commun* 465, 769-776 (2015).

What is claimed is:

1. A method for inducing interaction of a first protein with a second protein in a system, the method comprising providing a system comprising
(a) a first fusion protein comprising (i) a protein having the sequence of a *Rhodopseudomonas palustris* bacterial phytochrome RpBphP1 (BphP1) and (ii) the first protein, and
(b) a second fusion protein comprising (i) a protein having the sequence of a *Rhodopseudomonas palustris* transcriptional repressor RpPpsR2 (PpsR2) or a non-dimerizing variant thereof, wherein the non-dimerizing variant of PpsR2 has an amino acid sequence of SEQ ID NO:3 and (ii) the second protein, and
(c) an amount of biliverdin; and irradiating the system with near infrared light sufficient to induce interaction of a *Rhodopseudomonas palustris* BphP1 with a *Rhodopseudomonas palustris* PpsR2 or a non-dimerizing variant thereof, wherein the non-dimerizing variant of PpsR2 has an amino acid sequence of SEQ ID NO:3.

2. The method of claim 1, wherein the first or second protein is a DNA-binding protein.

3. The method of claim 1, wherein the first or second protein comprises a transcriptional activator protein.

4. The method of claim 1, wherein at least one of the first fusion protein and the second fusion protein further comprises a detectable marker protein or detectable marker peptide.

5. The method of claim 4, wherein the first fusion protein and the second fusion protein comprise different detectable marker proteins which are each fluorescent proteins.

6. The method of claim 1, wherein the system is a eukaryotic cell.

7. The method of claim 6, further comprising providing the system by transfecting the cell with a nucleic acid encoding the first fusion protein comprising a protein having the sequence of a *Rhodopseudomonas palustris* bacterial phytochrome RpBphP1 (BphP1).

8. The method of claim 6, further comprising providing the system by transfecting the cell with a nucleic acid encoding the second fusion protein comprising a protein having the sequence of a *Rhodopseudomonas palustris* transcriptional repressor RpPpsR2 (PpsR2) or a non-dimerizing variant thereof and the second protein.

9. A method for inducing translocation of a predetermined protein to a predetermined location in a cell comprising providing a system comprising
    (a) a first fusion protein comprising (i) a protein having the sequence of a *Rhodopseudomonas palustris* bacterial phytochrome RpBphP1 (BphP1) and (ii) a first protein,
    (b) a second fusion protein comprising (i) a protein having the sequence of a *Rhodopseudomonas palustris* transcriptional repressor RpPpsR2 (PpsR2) or a non-dimerizing variant thereof, wherein the non-dimerizing variant of PpsR2 has an amino acid sequence of SEQ ID NO:3 and (ii) a second protein, and
    (c) an amount of biliverdin, wherein one of the first and second proteins is the predetermined protein and wherein the other of the first and second proteins is a protein that preferentially locates to the predetermined location in a cell; and irradiating the system with near infrared light sufficient to induce interaction of a *Rhodopseudomonas palustris* BphP1 with a *Rhodopseudomonas palustris* PpsR2 or a non-dimerizing variant thereof, wherein the non-dimerizing variant of PpsR2 has an amino acid sequence of SEQ ID NO:3.

10. The method of claim 9, wherein the protein that preferentially locates to the predetermined location in a cell, preferentially locates to a plasma membrane of a cell.

11. The method of claim 9, wherein the protein that preferentially locates to the predetermined location in a cell, preferentially locates to an organelle of a cell.

12. The method of claim 9, wherein the protein that preferentially locates to the predetermined location in a cell, preferentially locates to a nucleus of a cell.

13. The method of claim 12, wherein the first fusion protein comprising the first protein or the second fusion protein comprising the second protein that preferentially locates to a nucleus, further comprises a DNA-binding protein.

14. The method of claim 12, wherein the first fusion protein comprising the first protein or the second fusion protein comprising the second protein that preferentially locates to a nucleus, further comprises a transcriptional activator protein.

15. The method of claim 9, wherein at least one of the first fusion protein and the second fusion protein further comprises a detectable marker protein or detectable marker peptide.

\* \* \* \* \*

SEQUENCE LISTING

<160> NUMBER OF SEQ ID NOS: 10

<210> SEQ ID NO 1
<211> LENGTH: 732
<212> TYPE: PRT
<213> ORGANISM: Rhodopseudomonas sp.

<400> SEQUENCE: 1

| | | | | | | | | | | | | | | |
|---|---|---|---|---|---|---|---|---|---|---|---|---|---|---|
| Met | Val | Gly | His | Ala | Ser | Gly | Ser | Pro | Ala | Phe | Gly | Thr | Ala | Asp |
| 1 | | | | 5 | | | | | 10 | | | | | 15 |
| Leu | Ser | Asn | Cys | Glu | Arg | Glu | Glu | Ile | His | Leu | Ala | Gly | Ser | Ile | Gln |
| | | | 20 | | | | | 25 | | | | | 30 | | |
| Pro | His | Gly | Ala | Leu | Leu | Val | Val | Ser | Glu | Pro | Asp | His | Arg | Ile | Ile |
| | | | 35 | | | | | 40 | | | | | 45 | | |
| Gln | Ala | Ser | Ala | Asn | Ala | Ala | Glu | Phe | Leu | Asn | Leu | Gly | Ser | Val | Leu |
| | 50 | | | | | 55 | | | | | 60 | | | | |
| Gly | Val | Pro | Leu | Ala | Glu | Ile | Asp | Gly | Asp | Leu | Leu | Ile | Lys | Ile | Leu |
| 65 | | | | | 70 | | | | | 75 | | | | | 80 |
| Pro | His | Leu | Asp | Pro | Thr | Ala | Glu | Gly | Met | Pro | Val | Ala | Val | Arg | Cys |
| | | | | 85 | | | | | 90 | | | | | 95 | |
| Arg | Ile | Gly | Asn | Pro | Ser | Thr | Glu | Tyr | Asp | Gly | Leu | Met | His | Arg | Pro |
| | | | | 100 | | | | | 105 | | | | | 110 | |
| Pro | Glu | Gly | Gly | Leu | Ile | Ile | Glu | Leu | Glu | Arg | Ala | Gly | Pro | Pro | Ile |
| | | | | 115 | | | | | 120 | | | | | 125 | |
| Asp | Leu | Ser | Gly | Thr | Leu | Ala | Pro | Ala | Leu | Glu | Arg | Ile | Arg | Thr | Ala |
| | 130 | | | | | 135 | | | | | 140 | | | | |
| Gly | Ser | Leu | Arg | Ala | Leu | Cys | Asp | Asp | Thr | Ala | Leu | Leu | Phe | Gln | Gln |
| 145 | | | | | 150 | | | | | 155 | | | | | 160 |
| Cys | Thr | Gly | Tyr | Asp | Arg | Val | Met | Val | Tyr | Arg | Phe | Asp | Glu | Gln | Gly |
| | | | | 165 | | | | | 170 | | | | | 175 | |
| His | Gly | Glu | Val | Phe | Ser | Glu | Arg | His | Val | Pro | Gly | Leu | Glu | Ser | Tyr |
| | | | | 180 | | | | | 185 | | | | | 190 | |
| Phe | Gly | Asn | Arg | Tyr | Pro | Ser | Ser | Asp | Ile | Pro | Gln | Met | Ala | Arg | Arg |
| | | | | 195 | | | | | 200 | | | | | 205 | |
| Leu | Tyr | Glu | Arg | Gln | Arg | Val | Arg | Val | Leu | Val | Asp | Val | Ser | Tyr | Gln |
| | 210 | | | | | 215 | | | | | 220 | | | | |
| Pro | Val | Pro | Leu | Glu | Pro | Arg | Leu | Ser | Pro | Leu | Thr | Gly | Arg | Asp | Leu |
| 225 | | | | | 230 | | | | | 235 | | | | | 240 |
| Asp | Met | Ser | Gly | Cys | Phe | Leu | Arg | Ser | Met | Ser | Pro | Ile | His | Leu | Gln |
| | | | | 245 | | | | | 250 | | | | | 255 | |
| Tyr | Leu | Lys | Asn | Met | Gly | Val | Arg | Ala | Thr | Leu | Val | Val | Ser | Leu | Val |
| | | | | 260 | | | | | 265 | | | | | 270 | |
| Val | Gly | Gly | Lys | Leu | Trp | Gly | Leu | Val | Ala | Cys | His | His | Tyr | Leu | Pro |
| | | | | 275 | | | | | 280 | | | | | 285 | |
| Arg | Phe | Ile | His | Phe | Glu | Leu | Arg | Ala | Ile | Cys | Glu | Leu | Leu | Ala | Glu |
| | | | | 290 | | | | | 295 | | | | | 300 | |
| Ala | Ile | Ala | Thr | Arg | Ile | Thr | Ala | Leu | Glu | Ser | Phe | Ala | Gln | Ser | Gln |
| 305 | | | | | 310 | | | | | 315 | | | | | 320 |
| Ser | Glu | Leu | Phe | Val | Gln | Arg | Leu | Glu | Gln | Arg | Met | Ile | Glu | Ala | Ile |
| | | | | 325 | | | | | 330 | | | | | 335 | |
| Thr | Arg | Glu | Gly | Asp | Trp | Arg | Ala | Ala | Ile | Phe | Asp | Thr | Ser | Gln | Ser |
| | | | | 340 | | | | | 345 | | | | | 350 | |
| Ile | Leu | Gln | Pro | Leu | His | Ala | Asp | Gly | Cys | Ala | Leu | Val | Tyr | Glu | Asp |
| | | | | 355 | | | | | 360 | | | | | 365 | |

Gln Ile Arg Thr Ile Gly Asp Val Pro Ser Thr Gln Asp Val Arg Glu
            370                 375                 380

Ile Ala Gly Trp Leu Asp Arg Gln Pro Arg Ala Ala Val Thr Ser Thr
385                 390                 395                 400

Ala Ser Leu Gly Leu Asp Val Pro Glu Leu Ala His Leu Thr Arg Met
                405                 410                 415

Ala Ser Gly Val Val Ala Ala Pro Ile Ser Asp His Arg Gly Glu Phe
                420                 425                 430

Leu Met Trp Phe Arg Pro Glu Arg Val His Thr Val Thr Trp Gly Gly
            435                 440                 445

Asp Pro Lys Lys Pro Phe Thr Met Gly Asp Thr Pro Ala Asp Leu Ser
            450                 455                 460

Pro Arg Arg Ser Phe Ala Lys Trp His Gln Val Val Glu Gly Thr Ser
465                 470                 475                 480

Asp Pro Trp Thr Ala Ala Asp Leu Ala Ala Ala Arg Thr Ile Gly Gln
                485                 490                 495

Thr Val Ala Asp Ile Val Leu Gln Phe Arg Ala Val Arg Thr Leu Ile
                500                 505                 510

Ala Arg Glu Gln Tyr Glu Gln Phe Ser Ser Gln Val His Ala Ser Met
            515                 520                 525

Gln Pro Val Leu Ile Thr Asp Ala Glu Gly Arg Ile Leu Leu Met Asn
530                 535                 540

Asp Ser Phe Arg Asp Met Leu Pro Ala Gly Ser Pro Ser Ala Val His
545                 550                 555                 560

Leu Asp Asp Leu Ala Gly Phe Phe Val Glu Ser Asn Asp Phe Leu Arg
                565                 570                 575

Asn Val Ala Glu Leu Ile Asp His Gly Arg Gly Trp Arg Gly Glu Val
                580                 585                 590

Leu Leu Arg Gly Ala Gly Asn Arg Pro Leu Pro Leu Ala Val Arg Ala
            595                 600                 605

Asp Pro Val Thr Arg Thr Glu Asp Gln Ser Leu Gly Phe Val Leu Ile
            610                 615                 620

Phe Ser Asp Ala Thr Asp Arg Arg Thr Ala Asp Ala Ala Arg Thr Arg
625                 630                 635                 640

Phe Gln Glu Gly Ile Leu Ala Ser Ala Arg Pro Gly Val Arg Leu Asp
                645                 650                 655

Ser Lys Ser Asp Leu Leu His Glu Lys Leu Leu Ser Ala Leu Val Glu
                660                 665                 670

Asn Ala Gln Leu Ala Ala Leu Glu Ile Thr Tyr Gly Val Glu Thr Gly
            675                 680                 685

Arg Ile Ala Glu Leu Leu Glu Gly Val Arg Gln Ser Met Leu Arg Thr
            690                 695                 700

Ala Glu Val Leu Gly His Leu Val Gln His Ala Ala Arg Thr Ala Gly
705                 710                 715                 720

Ser Asp Ser Ser Ser Asn Gly Ser Gln Asn Lys Lys
                725                 730

<210> SEQ ID NO 2
<211> LENGTH: 464
<212> TYPE: PRT
<213> ORGANISM: Rhodopseudomonas sp.

<400> SEQUENCE: 2

Met Ala Ser Lys Ser Val His Ala Asp Ile Thr Leu Leu Leu Asp Met
1               5                   10                  15

```
Glu Gly Val Ile Arg Glu Ala Thr Leu Ser Pro Thr Met Ala Ala Glu
             20                  25                  30

Ser Val Asp Gly Trp Leu Gly Arg Arg Trp Ser Asp Ile Ala Gly Ala
         35                  40                  45

Glu Gly Asp Lys Val Arg Arg Met Val Glu Asp Ala Arg Arg Ser
 50                  55                  60

Gly Ile Ser Ala Phe Arg Gln Ile Asn Gln Pro Phe Pro Ser Gly Val
 65                  70                  75                  80

Glu Ile Pro Ile Glu Phe Thr Thr Met Leu Leu Gly Asp Arg Thr Gly
                 85                  90                  95

Met Ile Ala Val Gly Lys Asn Met Gln Ala Val Thr Glu Leu His Ser
                100                 105                 110

Arg Leu Ile Ala Ala Gln Gln Ala Met Glu Arg Asp Tyr Trp Arg Leu
             115                 120                 125

Arg Glu Leu Glu Thr Arg Tyr Arg Leu Val Phe Asp Ala Ala Ala Asp
         130                 135                 140

Ala Val Met Ile Val Ser Ala Gly Asp Met Arg Ile Val Glu Ala Asn
145                 150                 155                 160

Arg Ala Ala Val Asn Ala Ile Ser Arg Val Glu Arg Gly Asn Asp Asp
                165                 170                 175

Leu Ala Gly Arg Asp Phe Leu Ala Glu Val Ala Ala Asp Arg Asp
                180                 185                 190

Ala Val Arg Asp Met Leu Ala Gln Val Arg Gln Arg Gly Thr Ala Leu
         195                 200                 205

Ser Val Leu Val His Leu Gly Arg Tyr Asp Arg Ala Trp Met Leu Arg
    210                 215                 220

Gly Ser Leu Met Ser Ser Glu Arg Arg Gln Val Phe Leu Leu His Phe
225                 230                 235                 240

Thr Pro Val Thr Thr Thr Pro Ala Ile Asp Asp Val Asp Asp Asp Ala
                245                 250                 255

Val Leu Arg Gly Leu Ile Asp Arg Ile Pro Asp Gly Phe Val Ala Leu
                260                 265                 270

Asp Ser Glu Gly Val Val Arg His Ala Asn Gln Ala Phe Leu Asp Leu
         275                 280                 285

Val Gln Ile Gly Ser Lys Pro Ala Ala Val Gly Arg Ser Leu Gly Val
    290                 295                 300

Trp Met Gly Arg Pro Gly Ala Asp Leu Ser Ser Leu Leu Thr Leu Leu
305                 310                 315                 320

Arg Arg Tyr Lys Thr Val Arg Leu Phe Gln Thr Thr Ile Arg Gly Glu
             325                 330                 335

Leu Gly Thr Glu Thr Glu Val Glu Val Ser Ala Val Asp Gly Glu Asp
         340                 345                 350

Asp Gln Tyr Ile Gly Val Leu Met Arg Asn Val Ala Arg Arg Leu Asp
    355                 360                 365

Ala Ala Asp Asp His Asp Ala Leu Arg Gln Ala Leu Gly Pro Ile Ser
         370                 375                 380

Lys Gln Leu Gly Arg Ser Ser Leu Arg Lys Leu Val Lys Asn Ala Val
385                 390                 395                 400

Ser Ile Val Glu Gln His Tyr Val Lys Glu Ala Leu Leu Arg Ser Lys
                405                 410                 415

Gly Asn Arg Thr Ala Thr Ala Glu Leu Leu Gly Leu Ser Arg Gln Ser
             420                 425                 430
```

```
Leu Tyr Ala Lys Leu Asn Ser Tyr Gly Phe Asp Asp Lys Gly Val Val
            435                 440                 445

Ala Ser Ala Ala Asp Gly Ala Glu Gly Ala Ser Asp Asp Ala Glu Asp
    450                 455                 460
```

<210> SEQ ID NO 3
<211> LENGTH: 464
<212> TYPE: PRT
<213> ORGANISM: Rhodopseudomonas sp.

<400> SEQUENCE: 3

```
Met Ala Ser Lys Ser Val His Ala Asp Ile Thr Leu Leu Asp Met
1               5                   10                  15

Glu Gly Val Ile Arg Glu Ala Thr Leu Ser Pro Thr Met Ala Ala Glu
                20                  25                  30

Ser Val Asp Gly Trp Leu Gly Arg Arg Trp Ser Asp Ile Ala Gly Ala
            35                  40                  45

Glu Gly Gly Asp Lys Val Arg Arg Met Val Glu Asp Ala Arg Arg Ser
    50                  55                  60

Gly Ile Ser Ala Phe Arg Gln Ile Asn Gln Pro Phe Pro Ser Gly Val
65              70                  75                  80

Glu Ile Pro Ile Glu Phe Thr Thr Met Leu Leu Gly Asp Arg Thr Gly
                85                  90                  95

Met Ile Ala Val Gly Lys Asn Met Gln Ala Val Thr Glu Leu His Ser
            100                 105                 110

Arg Leu Ile Ala Ala Gln Gln Ala Met Glu Arg Asp Tyr Trp Arg Leu
        115                 120                 125

Arg Glu Leu Glu Thr Arg Tyr Arg Leu Val Phe Asp Ala Ala Ala Asp
    130                 135                 140

Ala Val Met Ile Val Ser Ala Gly Asp Met Arg Ile Val Glu Ala Asn
145                 150                 155                 160

Arg Ala Ala Val Asn Ala Ile Ser Arg Val Glu Arg Gly Asn Asp Asp
                165                 170                 175

Leu Ala Gly Arg Asp Phe Leu Ala Glu Val Ala Ala Asp Arg Asp
            180                 185                 190

Ala Val Arg Asp Met Leu Ala Gln Val Arg Gln Arg Gly Thr Ala Leu
        195                 200                 205

Ser Val Leu Val His Leu Gly Arg Tyr Asp Arg Ala Trp Met Leu Arg
    210                 215                 220

Gly Ser Leu Met Ser Ser Glu Arg Arg Gln Val Phe Leu Leu His Phe
225                 230                 235                 240

Thr Pro Val Thr Thr Thr Pro Ala Ile Asp Asp Val Asp Asp Asp Ala
                245                 250                 255

Val Leu Arg Gly Leu Ile Asp Arg Ile Pro Asp Gly Phe Val Ala Leu
            260                 265                 270

Asp Ser Glu Gly Val Val Arg His Ala Asn Gln Ala Phe Leu Asp Leu
        275                 280                 285

Val Gln Ile Gly Ser Lys Pro Ala Ala Val Gly Arg Ser Leu Gly Val
    290                 295                 300

Trp Met Gly Arg Pro Gly Ala Asp Leu Ser Ser Leu Thr Leu Leu
305                 310                 315                 320

Arg Arg Tyr Lys Thr Val Arg Leu Phe Gln Thr Thr Ile Arg Gly Glu
                325                 330                 335

Leu Gly Thr Glu Thr Glu Val Glu Val Ser Ala Val Asp Gly Glu Asp
            340                 345                 350
```

Asp Gln Tyr Ile Gly Val Leu Met Arg Asn Val Ala Arg Arg Leu Asp
          355                 360                 365

Ala Ala Asp Asp His Asp Ala Leu Arg Gln Ala Leu Gly Pro Ile Ser
    370                 375                 380

Lys Gln Leu Gly Arg Ser Ser Leu Arg Lys Leu Val Lys Asn Ala Val
385                 390                 395                 400

Ser Ile Val Glu Gln His Tyr Val Lys Glu Ala Leu Leu Arg Ser Lys
                405                 410                 415

Gly Asn Arg Thr Ala Thr Ala Glu Leu Leu Gly Leu Ser Arg Gln Ser
            420                 425                 430

Leu Tyr Ala Lys Leu Asn Cys Tyr Gly Phe Asp Lys Gly Val Val
            435                 440                 445

Ala Ser Ala Ala Asp Gly Ala Glu Gly Ala Ser Asp Asp Ala Glu Asp
    450                 455                 460

<210> SEQ ID NO 4
<211> LENGTH: 24
<212> TYPE: PRT
<213> ORGANISM: Artificial Sequence
<220> FEATURE:
<223> OTHER INFORMATION: Chemically synthesized

<400> SEQUENCE: 4

Ser Gly Gly Gly Ser Gly Gly Gly Ser Gly Gly Ser Gly Gly
1               5                   10                  15

Ser Gly Gly Gly Ser Gly Gly Gly
            20

<210> SEQ ID NO 5
<211> LENGTH: 14
<212> TYPE: PRT
<213> ORGANISM: Rat sp.

<400> SEQUENCE: 5

Lys Lys Lys Lys Lys Lys Ser Lys Thr Lys Cys Val Ile Met
1               5                   10

<210> SEQ ID NO 6
<211> LENGTH: 20
<212> TYPE: PRT
<213> ORGANISM: Arabidopsis sp.

<400> SEQUENCE: 6

Met Ser Arg Arg Arg His Ser Tyr Glu Asn Asp Gly Gly Gln Pro His
1               5                   10                  15

Lys Arg Arg Lys
            20

<210> SEQ ID NO 7
<211> LENGTH: 18
<212> TYPE: PRT
<213> ORGANISM: Porcine sp.

<400> SEQUENCE: 7

Glu Gly Arg Gly Ser Leu Leu Thr Cys Gly Asp Val Glu Glu Asn Pro
1               5                   10                  15

Gly Pro

<210> SEQ ID NO 8
<211> LENGTH: 8

```
<212> TYPE: PRT
<213> ORGANISM: Artificial Sequence
<220> FEATURE:
<223> OTHER INFORMATION: Chemically synthesized

<400> SEQUENCE: 8

Trp Ser His Pro Gln Phe Glu Lys
1               5

<210> SEQ ID NO 9
<211> LENGTH: 2196
<212> TYPE: DNA
<213> ORGANISM: Rhodopseudomonas sp.

<400> SEQUENCE: 9
atggtggcag gtcatgcctc tggcagcccc gcattcggga ccgccgatct ttcgaattgc      60
gaacgtgaag agatccacct cgccggctcg atccagccgc atggcgcgct tctggtcgtc     120
agcgagccgg atcatcgcat catccaggcc agcgccaacg ccgcggaatt tctgaatctc     180
ggaagcgtgc tcggcgttcc gctcgccgag atcgacggcg atctgttgat caagatcctg     240
ccgcatctcg atcccaccgc cgaaggcatg ccggtcgcgg tgcgctgccg gatcggcaat     300
ccctccacgg agtacgacgg tctgatgcat cggcctccgg aagcgggct  gatcatcgag     360 ctcgaacgtg ccggcccgcc gatcgatctg tccggcacgc tggcgccggc gctggagcgg     420
atccgcacgc cgggctcgct cgcgcgcgtg tgcgatgaca ccgcgctgct gtttcagcag     480
tgcaccggct acgaccgggt gatggtgtat cgcttcgacg agcagggcca cggcgaagtg     540
ttctccgagc gccacgtgcc cgggctcgaa tcctatttcg caaccgcta  tccgtcgtcg     600 gacattccgc agatggcgcg gcggctgtac gagcggcagc gcgtccgcgt gctggtcgac     660
gtcagctatc agccggtgcc gctggagccg gctgtcgc   cgctgaccgg gcgcgatctc     720
gacatgtcgg gctgcttcct gcgctcgatg tcgccgatcc atctgcagta cctgaagaac     780
atgggcgtgc gcgccaccct ggtggtgtcg ctggtggtcg cggcaagct  gtggggcctg     840 gttgcctgtc accattatct gccgcgcttc atccatttcg agctgcgggc gatctgcgaa     900
ctgctcgccg aagcgatcgc gacgcggatc accgcgcttg agagcttcgc gcagagccag     960
tcggagctgt tcgtgcagcg gctcgaacag cgcatgatcg aagcgatcac ccgtgaaggc    1020
gattggcgcg cagcgatttt cgacaccagc caatcgatcc tgcagccgct gcacgccgac    1080
ggttgcgcgc tggtgtacga agaccagatc aggaccatcg gtgacgtacc ttccacgcag    1140
gatgttcgcg agatcgccgg gtggctcgat cgccagccac gtgcggcggt gacctcgacc    1200
gcgtcgctcg gtctcgacgt gccggagctc gcgcatctga cgcggatggc gagcggcgtg    1260
gtcgcggcgc cgatttcgga tcatcgcggc gagtttctga tgtggttccg ccccgagcgc    1320
gtccacaccg ttacctgggg cggcgatccg aagaagccgt tcacgatggg cgatacaccg    1380
gcggatctgt cgccgcggcg ctccttcgcc aaatggcatc aggttgtcga aggcacgtcc    1440
gatccgtgga cggccgccga tctcgccgcg gctcgcacca tcgtcagac  cgtcgccgac    1500 atcgtgctgc aattccgcgc ggtgcggaca ctgatcgccc gcgaacagta cgaacagttt    1560
tcgtcccagg tgcacgcttc gatgcagccg gtgctgatca ccgacgccga aggccgcatc    1620
ctgctgatga acgactcgtt ccgcgacatg ttgccggcgg ggtcgccatc cgccgtccat    1680
ctcgacgatc tcgccgggtt cttcgtcgaa tcgaacgatt tcctgcgcaa cgtcgccgaa    1740
ctgatcgatc acgccgcgg  gtggcgcggc gaagttctgc tgcgcggcgc aggtaatcgc    1800
ccgttgccgc tggcagtgcg cgccgatccg gtgacgcgca cggaggacca gtcgctcggc    1860
```

-continued

```
ttcgtgctga tcttcagcga cgctaccgat cgtcgcaccg cagatgccgc acgcacgcgt    1920
ttccaggaag gcattcttgc cagcgcacgt cccggcgtgc ggctcgactc caagtccgac    1980
ctcttgcacg agaagctgct gtccgcgctg gtcgagaacg cgcagcttgc cgcattggaa    2040
attacttacg gcgtcgagac cggacgcatc gccgagctgc tcgaaggcgt tcgccagtcg    2100
atgctgcgca ccgccgaagt gctcggccat ctggtgcagc acgcggcgcg cacggccggc    2160
agcgacagct cgagcaatgg ctcgcagaac aagaag                              2196
```

<210> SEQ ID NO 10
<211> LENGTH: 1392
<212> TYPE: DNA
<213> ORGANISM: Rhodopseudomonas sp.

<400> SEQUENCE: 10

```
gtggcgtcaa agtccgttca tgccgacatc acccttctgc tcgatatgga gggtgtgatt      60
cgcgaagcca ccctgtctcc gacgatggcg gccgagagcg tggacggttg gctggggcgt     120
cgctggagcg acatcgccgg cgccgaaggc ggcgacaagg ttcgccgcat ggtcgaagac     180
gcccgccgca gcggcatctc ggctttccgc cagatcaatc agccttttcc gagcggcgtc     240
gaaatcccga tcgaattcac cacgatgctg ctgggcgacc gcaccggcat gatcgcggtc     300
ggcaagaaca tgcaggcggt caccgagctg cattcccggc tgatcgctgc gcagcaggcg     360
atggagcgcg actattggcg gttgcgtgaa ttggagactc gctaccgcct ggtgttcgac     420
gctgccgccg atgcggtgat gatcgtctcc gccggcgaca tgcgcatcgt cgaagccaac     480
cgggcggcgg tgaatgcgat cagccgcgtc gagcgcggca atgacgacct tgcggggcgt     540
gatttcctcg ccgaagtggc ggctgccgat cgcgatgcgg tgcgcgacat gctggcccag     600
gtgcgtcagc gcggcaccgc actcagcgtc ctcgttcatc tcggccgtta cgaccgcgcc     660
tggatgctgc gcggttcgct gatgtcgtcc gagcgtcgtc aggttttcct gctgcacttc     720
accccggtga ccacgactcc cgcgatcgac gacgtcgacg atgatgccgt gctgcgcggg     780
ctgatcgatc gcattcccga cgggttcgtc gcactggatt cggaaggcgt cgttcgtcac     840
gccaaccagg cgtttctcga tctggtccag atcggctcca agcctgcggc ggtcggacga     900
tcgctgggcg tctggatggg tcgtccgggc gccgatctgt ccagcttgct gacgctgctg     960
cggcgctaca agacggtgcg gctgttccaa acgacgatcc gcggcgagct cggcaccgag    1020
actgaagtcg aggtctcggc cgtcgacggc gaggacgacc aatacatcgg cgttctgatg    1080
cgcaatgtcg cgcgacgcct cgacgctgcg gacgaccacg atgccttgcg tcaggcgctc    1140
ggcccgatca gcaagcagct cgggcgatcc tcgctgcgca agctggtgaa gaacgccgtg    1200
agcattgtcg agcagcacta cgtgaaggaa gcgctgttgc gatccaaggg caatcgcacg    1260
gcaactgccg aactgctcgg attgagccgg cagagccttt atgcaaaact caacagctac    1320
ggcttcgacg acaaaggtgt cgttgcttct gctgccgacg gtgcagaggg cgcctcagac    1380
gacgcagagg at                                                        1392
```